US011432551B2

(12) United States Patent
Bogosian

(10) Patent No.: US 11,432,551 B2
(45) Date of Patent: Sep. 6, 2022

(54) MICROBIAL FERMENTATION METHODS AND COMPOSITIONS

(71) Applicant: NewLeaf Symbiotics, Inc., St. Louis, MO (US)

(72) Inventor: Gregg Bogosian, Clarkson Valley, MO (US)

(73) Assignee: NewLeaf Symbiotics, Inc., St. Louis, MO (US)

( * ) Notice: Subject to any disclaimer, the term of this patent is extended or adjusted under 35 U.S.C. 154(b) by 56 days.

(21) Appl. No.: 16/906,554

(22) Filed: Jun. 19, 2020

(65) Prior Publication Data

US 2020/0318095 A1    Oct. 8, 2020

Related U.S. Application Data

(60) Division of application No. 16/566,108, filed on Sep. 10, 2019, now abandoned, which is a division of application No. 15/805,843, filed on Nov. 7, 2017, now Pat. No. 10,450,556, which is a division of application No. 14/876,431, filed on Oct. 6, 2015, now Pat. No. 9,845,462, which is a continuation of application No. 13/907,161, filed on May 31, 2013, now Pat. No. 9,181,541.

(60) Provisional application No. 61/784,375, filed on Mar. 14, 2013, provisional application No. 61/654,504, filed on Jun. 1, 2012, provisional application No. 61/654,394, filed on Jun. 1, 2012.

(51) Int. Cl.
| | |
|---|---|
| *A01N 63/20* | (2020.01) |
| *C12N 11/02* | (2006.01) |
| *C12N 1/20* | (2006.01) |
| *C12N 11/14* | (2006.01) |
| *C12N 11/16* | (2006.01) |

(52) U.S. Cl.
CPC .............. *A01N 63/20* (2020.01); *C12N 1/20* (2013.01); *C12N 11/02* (2013.01); *C12N 11/14* (2013.01); *C12N 11/16* (2013.01)

(58) Field of Classification Search
CPC .......... A01N 63/20; A01N 25/08; C12N 1/20; C12N 11/02; C12N 11/14; C12N 11/16
See application file for complete search history.

(56) References Cited

U.S. PATENT DOCUMENTS

| | | | |
|---|---|---|---|
| 6,107,067 A * | 8/2000 | Miller | .................... C12N 11/14 435/176 |
| 6,905,288 B2 | 6/2005 | Miyazaki | |
| 10,111,438 B2 | 10/2018 | Flora et al. | |
| 10,368,547 B2 | 8/2019 | Flora et al. | |
| 10,448,645 B2 | 10/2019 | Breakfield et al. | |
| 10,757,946 B2 | 9/2020 | Allen et al. | |
| 2019/0116803 A1 | 4/2019 | Flora et al. | |
| 2019/0297895 A1 | 10/2019 | Flora et al. | |
| 2019/0364905 A1 | 12/2019 | Rioux et al. | |
| 2019/0387747 A1 | 12/2019 | Breakfield et al. | |
| 2020/0115699 A1 | 4/2020 | Bogosian | |

FOREIGN PATENT DOCUMENTS

| | | |
|---|---|---|
| WO | 2020117689 A1 | 6/2020 |
| WO | 2020117690 A1 | 6/2020 |

OTHER PUBLICATIONS

Khongkhaem et al., Letters in Applied Microbiology, vol. 52, 2011, p. 448-455.*
Verhoef et al., Carbohydrate Research, 2003, vol. 338, p. 1851-1859.*
Urakami et al., International Journal of Systematic Bacteriology, Jul. 1993, vol. 43, No. 3, p. 504-513.*
"Bacteria Freeze Drying Protocol", OPS Diagnostics, 4 pages, http://www.opsdiagnostics.com/notes/ranpri/rpbacteriafdprotocol.htm, web pages downloaded on or before Jul. 3, 2014.
"Bacteria Lyophilization Overview", OPS Diagnostics, 3 pages, http://opsdiagnostics.com/notes/ranpri/bacteria_lyophilization_overview.htm, web pages downloaded on or before Jul. 3, 2014.
Guozheng Li et al. "2,4,5-Trichlorophenol Degradation Using a Novel TiO 2 —Coated Biofilm Carrier. Roles of Adsorption, Photocatalysis, and Biodegradation", Environmental Science & Technology, vol. 45, No. 19, Aug. 23, 2011, pp. 8359-8367, XP055074509, ISSN: 0013-936X, DOI: 10.1021/es2016523.
Tani et al., "*Methylobacterium* Species Promoting Rice and barley Growth and Interaction Specificity Revealed with Whole-Cell Matrix-Assisted Laser Desorption/Ionization-Time-of-Flight mass Spectrometry (MALDI-TOF/MS) Analysis". Jun. 8, 2015, PLOS ONE, 10(6)e0129509 pp. 1-15.
Ferrasym 402 Product sheet, @NewLeaf Symbiotics Jan. 2018, 2 pages.
Abanda-Nkpwatt et al., "Molecular interaction between Methylobacterium extorquens and seedlings: growth promotion, methanol consumption, and localization of the methanol emission site", Journal of Experimental Botany, vol. 57, No. 15, pp. 4025-4032, Oct. 16, 2006.
Instituto Nacional De La Propiedad Industrial in connection with Argentina Serial No. 20130101937 filed May 31, 2013, "Office Action", 7 pages, dated Aug. 25, 2020.

* cited by examiner

Primary Examiner — Kade Ariani
(74) Attorney, Agent, or Firm — McKee, Voorhees & Sease, PLC

(57) ABSTRACT

The present invention provides methods for the cultivation of the *Methylobacterium* genus of bacteria. In particular the method provides methods for the efficient and inexpensive cultivation of these bacteria. Additionally, the invention provides methods for the utilization of these bacterial cultures to improve plant agriculture.

18 Claims, 4 Drawing Sheets

FIGURE 3 A, B, C

MICROBIAL FERMENTATION METHODS AND COMPOSITIONS

CROSS-REFERENCE TO RELATED APPLICATIONS

This US non-provisional patent application is a divisional of U.S. patent application Ser. No. 16/566,108, filed Sep. 10, 2019, which is a divisional of U.S. patent application Ser. No. 15/805,843, filed Nov. 7, 2017, which is a divisional of U.S. patent application Ser. No. 14/876,431, filed Oct. 6, 2015, which is a continuation of U.S. patent application Ser. No. 13/907,161, filed May 31, 2013, now U.S. Pat. No. 9,181,541, issued Nov. 10, 2015, and incorporated herein by reference in its entirety; which claims the benefit of U.S. Patent Application No. 61/784,375, filed Mar. 14, 2013 and incorporated herein by reference in its entirety; U.S. Patent Application No. 61/654,504, filed Jun. 1, 2012 and incorporated herein by reference in its entirety; and U.S. Patent Application No. 61/654,394, filed Jun. 1, 2012 and incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers, unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

The existence of PPFM bacteria as colonizers of the leaf surfaces of most (if not all) species of plants (ranging from algae, mosses and liverworts, and angiosperms and gymnosperms) suggests that PPFM bacteria may play an important role in plant physiology (Corpe and Rheem, 1989; Holland and Polacco, 1994; Holland, 1997; Kutschera, 2007). The fact that plants produce and excrete methanol, probably as a waste product of pectin metabolism in growing plant cell walls, suggested to these researchers that a symbiotic relationship exists, with the PPFM bacteria feeding on the plant-produced methanol and in turn providing positive benefits to the plants. The suggested benefits of PPFM bacteria on plant physiology include positive effects on nitrogen metabolism, seed germination, and stimulation of plant growth through the provision of PPFM-generated cytokinin plant hormones. The use of PPFM bacteria to improve plant growth, plant yield, seed germination, male fertility, and plant nutritional qualities has been disclosed in U.S. Pat. Nos. 5,512,069, 5,961,687, 6,174,837, 6,329,320, 7,435,878, and US Patent Application Pub. No. 2006/0228797. In addition, PPFM bacteria have been found to increase the yield of cultivated algae, suggesting their application to the production of algae-derived biofuels (US Patent Application Pub. No. 2011/0269219).

SUMMARY

Provided herein are methods for efficient production of large quantities of *Methylobacterium*. These methods can result in high titer *Methylobacterium* cultures where production time per batch is significantly reduced. The methods of *Methylobacterium* production provided herein can also use culture medium comprised of inexpensive and readily available components. Also provide herein are useful fermentation broths, fermentation broth products, fermentation products, and compositions comprising *Methylobacterium*. Methods of using the fermentation broths, fermentation broth products, fermentation products, and compositions comprising *Methylobacterium* to treat plants or plant parts are also provided herein. The methods and compositions provided herein can be used to produce large quantities of *Methylobacterium* for application to plants or plant parts, for use as an inoculum in bioremediation, for production of useful products, and for production of recombinant proteins. Useful products obtainable by the methods and compositions provided herein include, but are not limited to, poly-3-hydroxy butyric acid, 1,3-propanediol, and oxazopyrroloquinolines.

Provided herein are fermentation broths comprising a liquid phase and a solid phase that can be suspended therein, wherein the solid phase comprises a solid substance wherein a mono-culture or co-culture of *Methylobacterium* is adhered thereto and wherein the fermentation broth is essentially free of contaminating microorganisms. In certain embodiments, the broth can further comprise one or more microorganisms of pre-determined identity other than *Methylobacterium*. In certain embodiments, the solid phase comprises at least about 0.02% to about 0.5% of the broth by mass. In certain embodiments, the solid substance is of animal, plant, microbial, fungal, or mineral origin. In certain embodiments, the solid substance is an agriculturally acceptable adjuvant or agriculturally acceptable excipient. In certain embodiments, the solid substance is a polymer. In certain embodiments, the solid substance comprises a polysaccharide, diatomaceous earth, or a salt crystal. In certain embodiments, the polysaccharide is selected from the group consisting of a cellulosic polysaccharide, a chitinous polysaccharide, and a galactan polysaccharide. In certain embodiments, the *Methylobacterium* are at a titer of at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter. In certain embodiments, the *Methylobacterium* are at a titer of at least about $5 \times 10^8$ colony-forming units per milliliter to at least about $6 \times 10^{10}$ colony-forming units per milliliter. In certain embodiments, at least one of the *Methylobacterium* is a Pink Pigmented Facultative Methylotroph (PPFM). In certain embodiments, the Pink Pigmented Facultative Methylotroph (PPFM) is selected from the group consisting of *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum, M. cerastii, M. gossipiicola, Methylobacterium* sp. strain LMG6378, *M. phyllosphaerae, M. oryzae, M. platani, M. populi,* and *M. zatmanii*. In certain embodiments, at least one of the *Methylobacterium* is *M. nodulans*. In certain embodiments of any of the aforementioned broths, at least 10% of the *Methylobacterium* in the fermentation broth are *Methylobacterium* that are adhered to the solid substance. In certain embodiments of any of the aforementioned broths, the solid is not a photosynthetic microorganism.

Also provided are fermentation broth products or fermentation products comprising a solid phase that can be suspended in liquid, wherein the solid phase comprises a solid substance wherein a mono-culture or co-culture of *Methylobacterium* is adhered thereto, and wherein the fermentation broth product or fermentation product is essentially free of contaminating microorganisms. In certain embodiments, the fermentation broth product or fermentation product further comprises one or more microorganisms of pre-determined identity other than *Methylobacterium*. In certain embodiments, the solid substance comprises a plurality of suspensible particles with adherent *Methylobacterium*. In certain embodiments, the solid substance is an agriculturally acceptable adjuvant or agriculturally acceptable excipient. In certain embodiments, the *Methylobacterium* titer of the solid phase is at least about $5 \times 10^8$ colony-forming units per gram to at least about $6 \times 10^{10}$ colony-forming units of *Methylobacterium* per gram of solid. In certain embodiments of any of the aforementioned fermentation broth products or fermentation products, the solid substance is not a photosynthetic microorganism.

Also provided are compositions comprising a plurality of particles that can be suspended in a liquid, wherein each of the particles comprise a solid substance wherein a mono-culture or co-culture of *Methylobacterium* is adhered thereto and wherein the solid substance is essentially free of contaminating microorganisms. In certain embodiments, the composition further comprises one or more microorganisms of pre-determined identity other than *Methylobacterium*. In certain embodiments, the solid substance comprises an agriculturally acceptable adjuvant or an agriculturally acceptable excipient. In certain embodiments, the composition further comprises at least one of an agriculturally acceptable adjuvant, an agriculturally acceptable excipient, and/or a pesticide. In certain embodiments, the composition is an essentially dry product, an emulsion, or a suspension. In certain embodiments, each of the particles is a particle of about 2 microns to about 1000 microns in average length or average diameter. In certain embodiments, the *Methylobacterium* titer of the particles is at least about $5 \times 10$ colony-forming units per gram to at least about $6 \times 10^{10}$ colony-forming units of *Methylobacterium* per gram of particles. In certain embodiments of any of the aforementioned compositions, the density of adherent *Methylobacterium* on the particles is at least about 1 *Methylobacterium*/20 square micrometers of particle surface area. In certain embodiments of any of the aforementioned compositions, the solid substance is not a photosynthetic microorganism.

Also provided are methods for culturing *Methylobacterium* comprising growing a mono-culture or co-culture of *Methylobacterium* in media that comprises a liquid phase and a solid phase that can be suspended therein, wherein the solid phase comprises a solid substance that provides for growth of the *Methylobacterium* and wherein the media is essentially free of contaminating microorganisms. In certain embodiments, the media further comprises one or more microorganisms of pre-determined identity other than *Methylobacterium*. In certain embodiments, the solid phase comprises at least about 0.02% to about 0.5% of the media by mass. In certain embodiments, the solid substance is an agriculturally acceptable adjuvant or agriculturally acceptable excipient. In certain embodiments, the solid substance provides for adherent growth of the *Methylobacterium*. In certain embodiments, the solid substance is a polymer or is of animal, plant, microbial, fungal, or mineral origin. In certain embodiments, the solid substance comprises a polysaccharide, diatomaceous earth, or a salt crystal. In certain embodiments, the polysaccharide is selected from the group of a cellulosic polysaccharide, a chitinous polysaccharide, and a galactan polysaccharide. In certain embodiments, the growing comprises the steps of inoculating the media with the *Methylobacterium* and incubating the inoculated media under conditions sufficient to provide for growth of the *Methylobacterium*. In certain embodiments, the *Methylobacterium* are inoculated into the media at a titer of at least about $5 \times 10^4$ colony-forming units per milliliter or at least about $1 \times 10^5$ colony-forming units per milliliter. In certain embodiments, the *Methylobacterium* is selected from the group consisting of *M. aminovorans, M. chloromethanicum, M. dichloromethanicum, M. extorquens, M. fujisawaense, M. mesophilicum, M. organophilum, M. radiotolerans, M. rhodesianum, M rhodinum, M. thiocyanatum, M. nodulans, M. cerastii, M. gossipiicola, Methylobacterium* sp. strain LMG6378, *M. phyllosphaerae, M. oryzae, M. platani, M. populi,* and *M. zatmanii*. In certain embodiments, at least 10% of the viable *Methylobacterium* in the fermentation broth are adherent *Methylobacterium*. In certain embodiments, a titer of at least about $5 \times 10^8$ colony-forming units per milliliter to about $6 \times 10^{10}$ colony-forming units per milliliter is attained. In certain embodiments, the titer of at least about $5 \times 10^8$ colony-forming units per milliliter to about $6 \times 10^{10}$ colony-forming units per milliliter is attained within about 48 hours, about 72 hours, or about 96 hours of inoculating the media with *Methylobacterium*. In certain embodiments of any of the aforementioned methods, the method further comprises the step of harvesting the *Methylobacterium*. In certain embodiments of any of the aforementioned methods, the solid substance is not a photosynthetic microorganism. Also provided are *Methylobacterium* mono-cultures or co-cultures obtained by any of the aforementioned methods. In certain embodiments, the mono-culture or co-culture of *Methylobacterium* is essentially free of contaminating microorganisms. Also provided are *Methylobacterium* culture products obtained from the *Methylobacterium* monoculture or co-culture obtained by the methods, wherein the *Methylobacterium* culture product comprises a plurality of particles that can be suspended in a liquid and the particles comprise a solid substance wherein a mono-culture or co-culture of *Methylobacterium* is adhered thereto. Also provided are compositions comprising the *Methylobacterium* culture product, fermentation broth product, or fermentation product. In certain embodiments, the culture product, fermentation broth product, or fermentation product comprises a mono-culture or co-culture of *Methylobacterium* that is essentially free of contaminating microorganisms. In certain embodiments, the composition further comprises an agriculturally acceptable adjuvant, an agriculturally acceptable excipient, and/or a pesticide. Also provided herein are methods for treating a plant or a plant part with *Methylobacterium* comprising the step of applying to the plant or plant part a *Methylobacterium* mono-cultures or co-culture, fermentation broth product, fermentation product, or composition obtained by any of the aforementioned methods. In certain embodiments of any of the aforementioned *Methylobacterium* mono-cultures or co-cultures, fermentation broth products, fermentation products, or compositions, the solid substance is not a photosynthetic microorganism.

Also provided are methods for treating a plant or a plant part with *Methylobacterium* comprising the step of applying to the plant or plant part a composition comprising a solid substance wherein a mono-culture or co-culture of *Methylobacterium* is adhered thereto. In certain embodiments, the mono-culture or co-culture of *Methylobacterium* is essentially free of contaminating microorganisms. In certain embodiments, the solid substance is an agriculturally acceptable adjuvant or an agriculturally acceptable excipient. In certain embodiments, the composition is an essentially dry product, an emulsion, or a suspension. In certain embodiments, the solid substance comprises a plurality of suspensible particles. In certain embodiments, each of the suspensible particles is a particle of about 2 microns to about 1000 microns in length or diameter. In certain embodiments, the plant part is a seed and the composition has a *Methylobacterium* titer of at least about $5\times10^1$ colony-forming units per gram to about $6\times10^{10}$ colony-forming units per gram of the composition. In certain embodiments, the *Methylobacterium* titer of the composition is at least about $5\times10^1$ colony-forming units per gram to at least about $6\times10^{10}$ colony-forming units of *Methylobacterium* per gram of the composition. In certain embodiments, the plant part is a seed, stem, root, flower, cotyledon, a coleoptile, or a leaf. In certain embodiments, the plant is a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, or conifer plant. In certain embodiments, the plant is a cereal plant and the part is a seed, a coleoptile, and/or a leaf. In certain embodiments, the plant is a cereal plant, the part is a seed, and the composition is applied in an amount sufficient to provide for an increase in nodal root growth in a cereal plant grown from the treated seed. In certain embodiments, the plant is a cereal plant, the part is a coleoptile, and/or a leaf, and the composition is applied in an amount sufficient to provide for an increase in nodal root growth in a cereal plant comprising the treated coleoptile and/or a leaf. In certain embodiments of any of the aforementioned methods, the cereal plant is selected from the group consisting of corn, barley, millet, oat, rice, rye, sorghum, Triticale, and wheat. In certain embodiments, the plant is a corn plant and the part is a seed, a coleoptile, and/or a leaf. In certain embodiments, the plant is a corn plant, the part is a seed, and the composition is applied in an amount sufficient to provide for an increase in corn nodal root growth in a corn plant grown from the treated seed. In certain embodiments, the plant is a corn plant, the part is a coleoptile, and/or a leaf, and the composition is applied in an amount sufficient to provide for an increase in corn nodal root growth in a corn plant comprising the treated coleoptile and/or a leaf. In certain embodiments of any of the aforementioned methods, the solid substance is not a photosynthetic microorganism. Also provided are plants or plant parts obtained by any of the aforementioned methods, wherein the plant or plant part is at least partially coated with an exogenously applied solid substance wherein a mono-culture or co-culture of *Methylobacterium* is adhered thereto. In certain embodiments, the plant part is a seed, stem, root, flower, cotyledon, a coleoptile, or a leaf. Also provided are processed plant products obtained from any of the aforementioned plants or plant parts, wherein the processed product contains an exogenous solid substance wherein a mono-culture or co-culture of *Methylobacterium* is adhered thereto. In certain embodiments, the plant product is a meal, paste, flour, flake, or feed. In certain embodiments, any of the aforementioned processed products is non-regenerable. In certain embodiments of any of the aforementioned plants, plant parts, or processed products, the solid substance is not a photosynthetic microorganism.

Also provided are methods for producing an industrial product comprising growing a mono-culture or co-culture of *Methylobacterium* in media that comprises a liquid phase and a solid phase that can be suspended therein, wherein the solid phase comprises a solid substance that provides for growth of the *Methylobacterium* and wherein the media is essentially free of contaminating microorganisms, and harvesting the industrial product from the solid phase, the liquid phase, or the combination thereof after growing the *Methylobacterium*. In certain embodiments, the solid substance provides for adherent growth of the *Methylobacterium*. In certain embodiments, the industrial product is a polymeric precursor, a biopolymer, a precursor of a medicinal compound, a medicinal compound, or a recombinant protein. In certain embodiments of any of the aforementioned methods, the industrial product is poly-3-hydroxy butyric acid, 1,3-propanediol, a pyrroloquinolinequinone, or an oxazopyrroloquinoline. In certain embodiments of any of the aforementioned methods, the solid substance is not a photosynthetic microorganism.

Also provided herein are methods for obtaining a *Methylobacterium* preparation comprising growing a mono-culture or co-culture of *Methylobacterium* in media that comprises a liquid phase and a solid phase, wherein the solid phase provides for increased yield of the *Methylobacterium* relative to yield obtained by growing the *Methylobacterium* in liquid media alone. In certain embodiments, the methods further comprise harvesting *Methylobacterium* grown in the media. In certain embodiments, at least substantially all of the solid phase is suspended in the liquid phase, or at least substantially all of the solid phase is not suspended in the liquid phase, or portions of the solid phase are suspended in the liquid phase and portions of the solid phase are not suspended in the liquid phase. In certain embodiments, the media further comprises one or more non-photosynthetic microorganisms of pre-determined identity other than *Methylobacterium*. In certain embodiments, the solid phase comprises at least about 0.02% to about 20% of the media by mass. In certain embodiments, the solid phase is an agriculturally acceptable adjuvant or agriculturally acceptable excipient. In certain embodiments, the solid phase provides for adherent growth of the *Methylobacterium* and/or the solid phase does not serve as a carbon source for the *Methylobacterium*. In certain embodiments, the solid phase comprises a solid substance selected from the group consisting of a man-made material, a material of animal origin, a material of plant origin, a material of microbial origin, a material of fungal origin, a material of mineral origin, and combinations thereof. In certain embodiments, the solid substance is inanimate. In certain embodiments, the solid phase comprises a solid substance selected from the group consisting of a polysaccharide, a diatomaceous earth, a salt crystal, and combinations thereof. In certain embodiments, the solid phase comprises a polysaccharide is selected from the group of a cellulosic polysaccharide, a chitinous polysaccharide, and a galactan polysaccharide. In certain embodiments, growing the mono-culture or co-culture of *Methylobacterium* comprises the steps of inoculating the media with the *Methylobacterium* and incubating the inoculated media under conditions sufficient to provide for growth of the *Methylobacterium*. In certain embodiments, either: (i) the solid phase comprises at least about 0.02% to about 0.5% of the media and substantially all of the solid phase is suspended in the liquid phase; or (ii) the solid phase comprises at least about 0.02% to about 20% of the media and: (a) substantially all of the solid phase is not suspended in the liquid phase; or (b) portions of the solid phase are suspended in the liquid phase and portions of the solid phase are not suspended in the liquid phase. In certain embodiments, the *Methylobacterium* is selected from the group consisting of *M. aminovorans, M. chloromethanicum, M. dichloromethanicum, M. extorquens, M. fujisawaense, M. mesophilicum, M. organophilum, M radiotolerans, M. rhodesianum, M. rhodinum, M. thiocyanatum, M. nodulans, M. cerastii, M. gossipiicola, Methylobacterium* sp. strain LMG6378, *M. phyllosphaerae, M. oryzae, M. platani, M. populi*, and *M. zatmanii*. In certain embodiments, at least 10% of the viable *Methylobacterium* in the fermentation broth are *Methylobacterium* that are adhered to the solid phase. In certain embodiments, the solid substance is not a photosynthetic microorganism, and/or the media is essentially free of contaminating microorganisms. In certain embodiments, the harvesting comprises recovering all or a portion of the solid phase with *Methylobacterium* adhered thereto and/or recovering all or a portion of non-adherent *Methylobacterium* from the liquid phase. In certain embodiments, the methods further comprise disassociating some or all of the solid phase with *Methylobacterium* adhered thereto. In certain embodiments, the methods further comprise drying the disassociated or partially disassociated material. In certain embodiments, the methods further comprise: i) drying the solid phase with *Methylobacterium* adhered thereto that had been separated from the liquid phase; or, ii) drying the solid phase with *Methylobacterium* adhered thereto and non-adherent *Methylobacterium* that were recovered from the liquid phase. In certain embodiments, the methods further comprise disassociating some or all of either: i) the dried solid phase with *Methylobacterium* adhered thereto; or, ii) the dried solid phase with *Methylobacterium* adhered thereto and non-adherent *Methylobacterium*.

Also provided are *Methylobacterium* preparations obtained by any of the aforementioned methods, wherein the *Methylobacterium* preparation comprises the solid substance wherein a mono-culture or co-culture of *Methylobacterium* is adhered thereto. In certain embodiments, the solid substance in the preparation is not a photosynthetic microorganism.

Also provided are methods for treating a plant or a plant part with *Methylobacterium* that comprise the step of applying to the plant or plant part a composition comprising the *Methylobacterium* preparation made by any of the aforementioned methods. In certain embodiments of the methods, the composition further comprises an agriculturally acceptable adjuvant or an agriculturally acceptable excipient. In certain embodiments of the methods, the composition is an essentially dry product, an emulsion, or a suspension. In certain embodiments of the methods, the plant part is a seed and the composition has a *Methylobacterium* titer of at least about $5\times10^8$ colony-forming units per gram of the composition to about $6\times10^{10}$, $3\times10^{12}$, $5\times10^{12}$, $1\times10^{13}$, or $5\times10^{13}$ colony-forming units per gram of the composition. In certain embodiments of the methods, the plant part is a seed, stem, root, flower, cotyledon, a coleoptile, a fruit, or a leaf. In certain embodiments of the methods, the plant or plant part is a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, or conifer plant part.

Also provided are plants or plant parts obtained by any of the aforementioned methods, wherein the plant or plant part is at least partially coated with an exogenous solid substance wherein a mono-culture or co-culture of *Methylobacterium* is adhered thereto. Processed plant products obtained from the plants or plant parts obtained by any of the aforementioned methods, wherein the processed product contains an exogenous solid substance wherein a mono-culture or co-culture of *Methylobacterium* is adhered thereto are also provided. In certain embodiments, the processed plant product is a meal, paste, flour, flake, or feed. In certain embodiments, the processed plant product is non-regenerable.

Also provided are methods for obtaining a *Methylobacterium* preparation comprising: (i) growing a mono-culture or co-culture of *Methylobacterium* in either: (a) a culture vessel that comprises or contains one or more solid surfaces that provide for adherent growth of the *Methylobacterium*; or, (b) media that comprises a liquid phase and a solid phase, wherein the solid phase provides for increased yield of the *Methylobacterium* relative to yield obtained by growing the *Methylobacterium* in liquid media alone; and, (ii) harvesting *Methylobacterium* adhered to the solid surface or the solid phase. In certain embodiments of the methods, harvesting comprises removal of the *Methylobacterium* from the solid surface or the solid phase by of exposing the *Methylobacterium* to one or more of a physical and/or a chemical treatment.

In certain embodiments of the methods, the chemical treatment comprises one or more of an ionic strength shift, a pH shift, a detergent treatment, a solvent treatment, and/or an enzymatic treatment. In certain embodiments of the methods, the enzymatic treatment comprises exposing *Methylobacterium* adhered to the solid surface or to the solid phase to a protease, a lipase, a glucanase, or any combination thereof. In certain embodiments of the methods, the detergent treatment comprises exposing *Methylobacterium* adhered to the solid surface or the solid phase to an ionic detergent, a non-ionic detergent, or any combination thereof. In certain embodiments of the methods, the physical treatment comprises exposing *Methylobacterium* adhered to the solid surface or to the solid phase to sonication, scraping, a pressurized liquid, a pressurized slurry, heat, or any combination thereof. In certain embodiments of the methods: (i) at least substantially all of the solid phase is suspended in the liquid phase; or (ii) at least substantially all of the solid phase is not suspended in the liquid phase; or (iii) portions of the solid phase are suspended in the liquid phase and portions of the solid phase are not suspended in the liquid phase. In certain embodiments of the methods, the solid phase provides for adherent growth of the *Methylobacterium* and/or the solid phase does not serve as a carbon source for the *Methylobacterium*. In certain embodiments of the methods, the solid phase comprises a solid substance selected from the group consisting of a man-made material, a material of animal origin, a material of plant origin, a material of microbial origin, a material of fungal origin, a material of mineral origin, and combinations thereof. In certain embodiments of the methods, the solid substance is inanimate. In certain embodiments of the methods, the solid phase comprises a solid substance selected from the group consisting of a polysaccharide, a diatomaceous earth, a salt crystal, and combinations thereof. In certain embodiments of the methods, the polysaccharide is selected from the group of a cellulosic polysaccharide, a chitinous polysaccharide, and a galactan polysaccharide. In certain embodiments of any of the aforementioned method, the methods can further comprise the step of drying the harvested *Methylobacterium*.

Also provided herein are fermentation products comprising a solid substance wherein a mono-culture or co-culture of *Methylobacterium* is adhered thereto, wherein the solid substance is not a photosynthetic microorganism, and wherein the fermentation product is essentially free of contaminating microorganisms. In certain embodiments, the fermentation product further comprises one or more microorganisms of pre-determined identity other than *Methylobacterium*. In certain embodiments, the solid substance comprises one or more of: (i) a plurality of suspensible particles with adherent *Methylobacterium*; (ii) a solid substance that cannot be suspended in fermentation broth; or (iii) a solid substance wherein a portion of the substance can be suspended in fermentation broth and a portion of the substance cannot be suspended in fermentation broth. In certain embodiments, the solid substance is inanimate. In certain embodiments, the solid substance is selected from the group consisting of a man-made material, a material of animal origin, a material of plant origin, a material of microbial origin, a material of fungal origin, a material of mineral origin, and combinations thereof. In certain embodiments, the solid substance is selected from the group consisting of a polysaccharide, a diatomaceous earth, a salt crystal, and combinations thereof. In certain embodiments, the polysaccharide is selected from the group of a cellulosic polysaccharide, a chitinous polysaccharide, and a galactan polysaccharide. In certain embodiments, the solid substance is an agriculturally acceptable adjuvant or agriculturally acceptable excipient. In certain embodiments of any of the aforementioned fermentation products, the *Methylobacterium* titer of the solid phase is at least about $5 \times 10^8$ colony-forming units per gram of solid to at least about $6 \times 10^{10}$, $3 \times 10^{12}$, $5 \times 10^{12}$, $1 \times 10^{13}$, or $5 \times 10^{13}$ colony-forming units of *Methylobacterium* per gram of solid. In certain embodiments of any of the aforementioned fermentation products, the density of adherent *Methylobacterium* on the solid substance is at least about 1 *Methylobacterium*/20 square micrometers of particle surface area.

Also provided are compositions that comprise a fermentation product comprising a solid substance wherein a mono-culture or co-culture of *Methylobacterium* is adhered thereto. In certain embodiments, the composition further comprises at least one of an agriculturally acceptable adjuvant and/or an agriculturally acceptable excipient. In certain embodiments, the solid substance comprises a plurality of particles with *Methylobacterium* adhered thereto. In certain embodiments, the particles comprise particles of about 2 microns to about 1000 microns in average length or average diameter. In certain embodiments, the *Methylobacterium* titer of the particles is at least about $5 \times 10^8$ colony-forming units per gram of particles to at least about $6 \times 10^{10}$, $3 \times 10^{12}$, $5 \times 10^{12}$, $1 \times 10^{13}$, or $5 \times 10^{13}$ colony-forming units of *Methylobacterium* per gram of particles. In certain embodiments, the solid substance is inanimate. In certain embodiments, the solid substance is selected from the group consisting of a man-made material, a material of animal origin, a material of plant origin, a material of microbial origin, a material of fungal origin, a material of mineral origin, and combinations thereof. In certain embodiments, the solid substance is selected from the group consisting of a polysaccharide, a diatomaceous earth, a salt crystal, and combinations thereof. In certain embodiments, the polysaccharide is selected from the group of a cellulosic polysaccharide, a chitinous polysaccharide, and a galactan polysaccharide. In certain embodiments, the solid substance is essentially free of contaminating microorganisms. In certain embodiments, the composition is essentially free of contaminating microorganisms. In certain embodiments, the composition and/or the solid substance can further comprise one or more microorganisms of pre-determined identity other than *Methylobacterium*. In certain embodiments, the solid substance comprises an agriculturally acceptable adjuvant or an agriculturally acceptable excipient. In certain embodiments, the solid substance is not a photosynthetic microorganism. In certain embodiments, the composition further comprises at least one pesticide and/or at least one bacteriostatic agent. In certain embodiments, the pesticide is selected from the group consisting of an insecticide, a fungicide, a nematocide, and a bacteriocide, wherein the pesticide does not substantially inhibit growth of the *Methylobacterium*. In certain embodiments, the composition is an essentially dry product, an emulsion, or a suspension. In certain embodiments, the density of adherent *Methylobacterium* on the solid substance is at least about 1 *Methylobacterium*/20 square micrometers of particle surface area.

Also provided herein are methods for treating a plant or a plant part with *Methylobacterium* comprising the step of applying to the plant or plant part any of the aforementioned compositions. In certain embodiments, the plant part is a seed, stem, root, flower, cotyledon, a coleoptile, fruit, or a leaf. In certain embodiments, the plant or plant part is a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, or conifer plant or plant part. Also provided are plants obtained by any of the aforementioned methods, wherein the plant is at least partially coated with the fermentation product of the composition. In certain embodiments, the plant is a corn plant, the part is a seed, and the composition is applied in an amount sufficient to provide for an increase in corn nodal root growth in a corn plant grown from the treated seed. In certain embodiments, the plant is a corn plant, the part is a coleoptile, and/or a leaf, and said composition is applied in an amount sufficient to provide for an increase in corn nodal root growth in a corn plant comprising the treated coleoptile and/or leaf. Also provided are plant parts obtained by any of the aforementioned methods, wherein the plant part is at least partially coated with the fermentation product of the composition. In certain embodiments, the plant part is a seed, stem, root, flower, cotyledon, a coleoptile, fruit, or a leaf.

Also provided are plants that are at least partially coated with a fermentation product comprising a solid substance wherein a mono-culture or co-culture of *Methylobacterium* is adhered thereto. In certain embodiments, the plant is selected from the group consisting of a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, and conifer plant. In certain embodiments, the solid substance comprises a plurality of particles with adherent *Methylobacterium*. In certain embodiments, the particles are about 2 microns to about 1000 microns in average length or average diameter. In certain embodiments, the *Methylobacterium* titer of the particles is at least about $5 \times 10^8$ colony-forming units per gram of particles to at least about $6 \times 10^{10}$, $3 \times 10^{12}$, $5 \times 10^{12}$, $1 \times 10^{13}$, or $5 \times 10^{13}$ colony-forming units of *Methylobacterium* per gram of particles. In certain embodiments, the density of adherent *Methylobacterium* on the solid substance is at least about 1 *Methylobacterium*/20 square micrometers of particle surface area. In certain embodiments, the solid substance is inanimate. In certain embodiments, the solid substance is selected from the group consisting of a man-made material, a material of animal origin, a material of plant origin, a material of microbial origin, a material of fungal origin, a material of mineral origin, and combinations thereof. In certain embodiments, the solid substance is selected from the group consisting of a polysaccharide, a diatomaceous earth, a salt crystal, and combinations thereof. In certain embodiments, the polysaccharide is selected from the group of a cellulosic polysaccharide, a chitinous polysaccharide, and a galactan polysaccharide. In certain embodiments, the solid substance is essentially free of contaminating microorganisms. In certain embodiments, the solid substance further comprises one or more microorganisms of pre-determined identity other than *Methylobacterium*. In certain embodiments, the solid substance comprises an agriculturally acceptable adjuvant or an agriculturally acceptable excipient. In certain embodiments, the solid substance is not a photosynthetic microorganism.

Also provided are plant parts that are at least partially coated with a composition that comprises a fermentation product comprising a solid substance wherein a mono-culture or co-culture of *Methylobacterium* is adhered thereto. In certain embodiments, the plant part is selected from the group consisting of a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, and conifer plant part. In certain embodiments, the solid substance comprises a plurality of particles with adherent *Methylobacterium*. In certain embodiments, the particles comprise particles of about 2 microns to about 1000 microns in average length or average diameter. In certain embodiments, the *Methylobacterium* titer of the particles is at least about $5 \times 10^1$ colony-forming units per gram of particles to at least about $6 \times 10^{10}$, $3 \times 10^{12}$, $5 \times 10^{12}$, $1 \times 10^{13}$, or $5 \times 10^{13}$ colony-forming units of *Methylobacterium* per gram of particles. In certain embodiments, the density of adherent *Methylobacterium* on the solid substance is at least about 1 *Methylobacterium*/20 square micrometers of particle surface area. In certain embodiments, the solid substance is inanimate. In certain embodiments, the solid substance is selected from the group consisting of a man-made material, a material of animal origin, a material of plant part origin, a material of microbial origin, a material of fungal origin, a material of mineral origin, and combinations thereof. In certain embodiments, the solid substance is selected from the group consisting of a polysaccharide, a diatomaceous earth, a salt crystal, and combinations thereof. In certain embodiments, the polysaccharide is selected from the group of a cellulosic polysaccharide, a chitinous polysaccharide, and a galactan polysaccharide. In certain embodiments, the solid substance is essentially free of contaminating microorganisms. In certain embodiments, the solid substance further comprises one or more microorganisms of pre-determined identity other than *Methylobacterium*. In certain embodiments, the solid substance comprises an agriculturally acceptable adjuvant or an agriculturally acceptable excipient. In certain embodiments, the solid substance is not a photosynthetic microorganism. In certain embodiments, the composition further comprises at least one pesticide. In certain embodiments, the pesticide is selected from the group consisting of an insecticide, a fungicide, a nematocide, and a bacteriocide, wherein the pesticide does not inhibit the *Methylobacterium*. In certain embodiments of any of the aforementioned embodiments, the plant part is a seed.

Also provided are processed plant products obtained from any of the aforementioned plants or plant parts, wherein the processed product contains a detectable amount of an exogenous solid substance wherein a mono-culture or co-culture of *Methylobacterium* is adhered thereto. In certain embodiments, the processed product is a meal, paste, flour, flake, or feed. In certain embodiments, the processed product is non-regenerable.

BRIEF DESCRIPTION OF THE DRAWINGS

The accompanying drawings, which are incorporated in and form a part of the specification, illustrate certain embodiments of the present invention. In the drawings.

DESCRIPTION

Definitions

Figure 1:
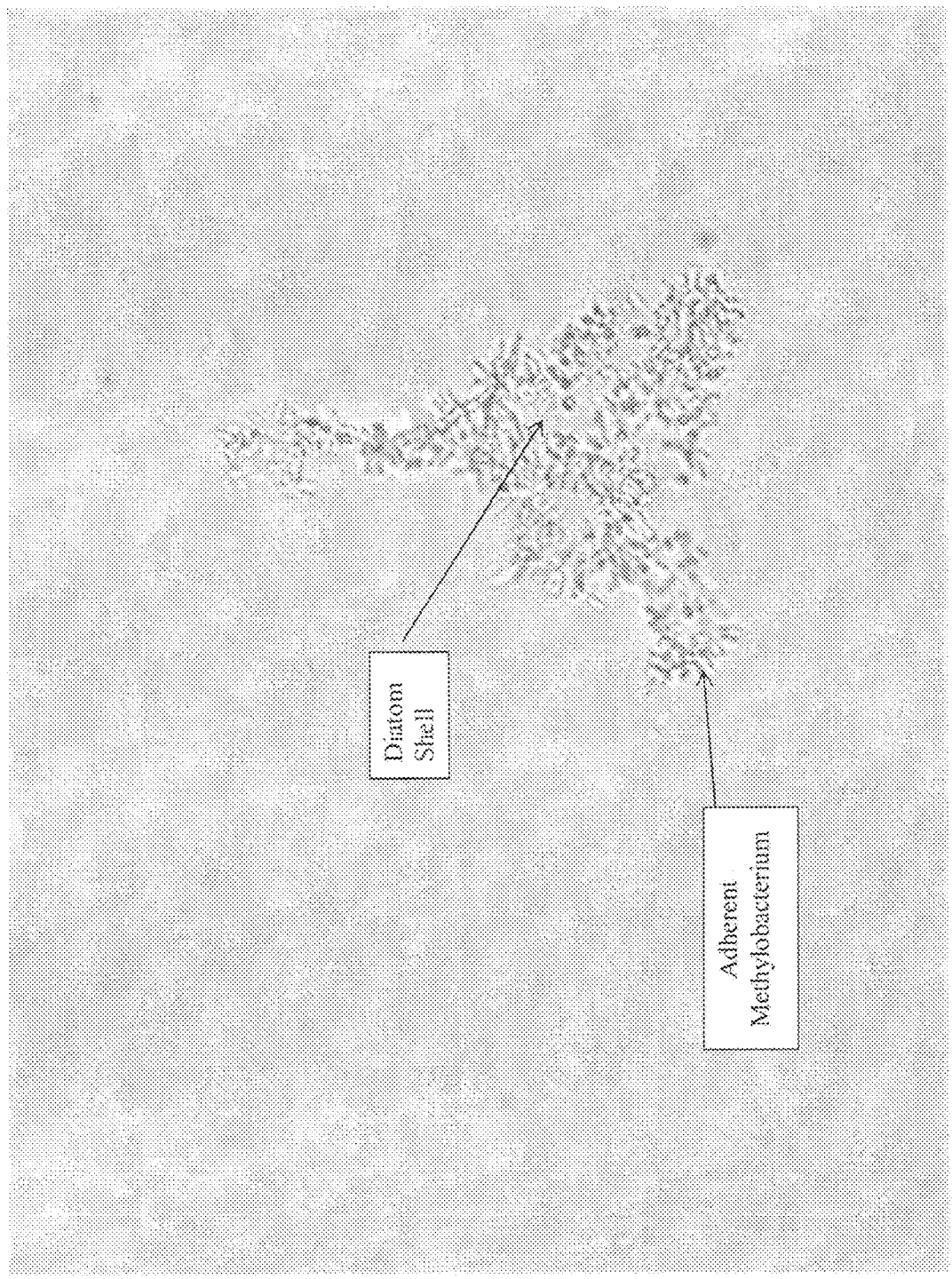
FIG. 1 is a photomicrograph of an aliquot of a fermentation product comprising liquid media, a solid (diatom shells), and *Methylobacterium*. The solid diatom shell and adherent *Methylobacterium* are indicated by the labels in the photomicrograph. The *Methylobacterium* strain is DSM-6343 *Methylobacterium* extorquens.

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants. In certain compositions, an active agent can comprise a mono-culture or co-culture of *Methylobacterium*.

As used herein, the term "algae" refers to any type of micro- or macroalgae.

As used herein, the term "*Methylobacterium*" refers to bacteria that are facultative methylotrophs of the genus *Methylobacterium*. The term *Methylobacterium*, as used herein, thus does not encompass include species in the genera *Methylobacter, Methylomonas, Methylomicrobium, Methylococcus, Methylosinus, Methylocystis, Methylosphaera, Methylocaldum,* and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

As used herein, the term "yield", when used in reference to *Methylobacterium* obtained in a fermentation, refers to the numbers of *Methylobacterium* obtained. Methods for determining such yield include, but are not limited to, determining the numbers of colony forming units (CFU) per unit volume or unit mass of material obtained, determining a wet weight of the *Methylobacterium* obtained, and/or determining a dry weight of the *Methylobacterium* obtained.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Methods for Culturing *Methylobacterium*, Compositions, and Uses Thereof

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). The methods can also further comprise the steps of harvesting the mono- or co-culture of *Methylobacterium*. Methods for harvesting the *Methylobacterium* can include, but are not limited to, separating the *Methylobacterium* from the liquid phase by filtration, centrifugation, decanting, and the like. Harvested *Methylobacterium* obtained by these methods can be *Methylobacterium* that are adhered to the solid substance, *Methylobacterium* that are not adhered to the solid substance, and combinations thereof.

Agitation methods that can be used include, but are not limited to, stirring, reciprocal shaking, rotary shaking, and combinations thereof. In certain embodiments, agitation can comprise placing liquid media containing the solid substances on a rotary shaker that provides at least 25, 50, 100, 200, 250, 500, or 1000 revolutions per minute (RPM). Agitation equivalent to that provided by a rotary shaker set at least at 25, 50, 100, 200, 250, 500, or 1000 revolutions per minute (RPM) can also be obtained by stirring, reciprocal shaking, and other methods. In certain embodiments, at least substantially all of the solid phase, or a portion of the solid phase, can be suspended in the liquid phase upon agitation equivalent to that provided by a rotary shaker set at least at 25, 50, 100, 200, 250, 500, or 1000 revolutions per minute (RPM).

In certain embodiments, harvested material comprising a solid substance with *Methylobacterium* adhered thereto can be disassociated. Dissociation can be effected by any techniques that permit the solid substance with *Methylobacterium* adhered thereto to be broken into smaller elements. Disassociation techniques including, but are not limited to, macerating, grinding, crushing, sonicating, and/or partially dissolving the solid substance with *Methylobacterium* adhered thereto can be used to break the solid substance with *Methylobacterium* adhered thereto into smaller elements. Such smaller elements include, but are not limited to, non-particulate solid substances with *Methylobacterium* adhered thereto and particles of the solid substance with *Methylobacterium* adhered thereto. Such non-particulate and/or particulate solid substances with *Methylobacterium* adhered thereto can either be directly applied to plants or plant parts or incorporated into compositions that can be applied to plants or plant parts. In certain embodiments, the solid substances with *Methylobacterium* adhered thereto are broken into particles of about 1 millimeter in diameter or less. In certain embodiments, a harvested solid substance with *Methylobacterium* adhered thereto is disassociated into particles of about 2 microns to about 1000 microns in average length or average diameter. In certain embodiments, a harvested solid substance with *Methylobacterium* adhered thereto is disassociated into particles of about 1 microns to about 1000 microns in average length or average diameter. In certain embodiments, a harvested solid substance with *Methylobacterium* adhered thereto is disassociated into particles of about 1, 2, 4, 10, 20, or 40 microns to any of about 100, 200, 500, 750, or 1000 microns in average length or average diameter. In certain embodiments, the *Methylobacterium* titer of the particles obtained by disassociation is at least about $5\times10^8$ colony-forming units per gram of particles to at least about $6\times10^{10}$, $3\times10^{12}$, $5\times10^{12}$, $1\times10^{13}$, or $5\times10^{13}$ colony-forming units of *Methylobacterium* per gram of particles. In certain embodiments, a solid substance with *Methylobacterium* adhered thereto will also comprise non-adherent *Methylobacterium*. In certain embodiments, solid substances that further comprising both adherent *Methylobacterium* and non-adherent *Methylobacterium* can also be disassociated to obtain any of the aforementioned fragments or particles. In still other embodiments, solid substances with *Methylobacterium* adhered thereto can be disassociated and non-adherent *Methylobacterium* can then be added to the disassociated solid substances comprising adherent *Methylobacterium*.

Solid substances with *Methylobacterium* adhered thereto can be disassociated when they are in either a wet or moist form or a dry form. Drying of the solid substance with *Methylobacterium* can be effected by any technique that maintains viability of the majority of the adherent *Methylobacterium*, and, when present, non-adherent *Methylobacterium*. Such drying techniques include, but are not limited to, lyophilization, desiccation, heating, and combinations thereof. In certain embodiments, drying can be thus effected after disassociation of a solid substance with *Methylobacterium* adhered thereto to obtain fragments or particles of the solid substance with *Methylobacterium* adhered thereto. In other embodiments, a solid substance with *Methylobacterium* adhered thereto, or a solid substance further comprising both adherent *Methylobacterium* and non-adherent *Methylobacterium*, can be dried and then dissociated. In certain embodiments where the solid substance with *Methylobacterium* adhered thereto, or a solid substance further comprising both adherent *Methylobacterium* and non-adherent *Methylobacterium*, is dried and then disassociated, solid substances that become friable upon drying can be used as the solid substance in the *Methylobacterium* fermentation process. Examples of such solid substances that become friable upon drying and that can be used in methods provided herein include, but are not limited to, certain materials of plant origin (e.g. certain materials comprising cellulose, hemi-cellulose, and/or lignin), and the like.

Biphasic fermentation broths used in the methods provided herein can be axenic cultures that are essentially free of contaminating microorganisms. In certain embodiments, at least about 95%, 98%, 99%, 99.5%, 99.8%, 99.9%, or 100% of the microorganisms present by amount or type in the culture, fermentation broth, fermentation product, or compositions provided herein are the desired *Methylobacterium* or other desired microorganisms of pre-determined identity. Desired *Methylobacterium* or other desired microorganisms of pre-determined identity are microorganisms obtained from a pure culture. To provide for such axenic cultures, the liquid and solid components used in the biphasic culture media are sterilized or obtained in an essentially sterile form prior to inoculation of *Methylobacterium* and/or any additional desired microorganisms in the mono- or co-culture. Sterilization of various solid and liquid components can be achieved by methods including, but not limited to, autoclaving, irradiation, filter sterilization (for liquids), and the like. A culture, fermentation broth, fermentation product, or composition that is essentially free of contaminating microorganisms can be obtained where the liquid and/or solid components of that culture, fermentation broth, fermentation product, or composition were sterile prior to the inoculation or provision of the desired microorganisms of pre-determined identity and suitable steps are taken to avoid contamination of the culture during growth of the desired microorganisms or contamination of the composition.

Methods provided herein where *Methylobacterium* are cultured in biphasic media comprising a liquid phase and a solid substance can be practiced in any of a batch-mode fermentation, a fed-batch mode fermentation, or a continuous fermentation. Fermentation broths, fermentation broth products, and compositions provided herein can also be obtained from any of a batch-mode fermentation, a fed-batch mode fermentation, or a continuous fermentation. In certain embodiments, factors such as the pH and oxygen concentration can be controlled in any of the batch-mode fermentation, fed-batch mode fermentation, or continuous fermentation processes used in the methods provided herein.

Monocultures or co-cultures of *Methylobacterium* and resultant fermentation broths and fermentation broth products provided herein can comprise one or more *Methylobacterium* that include, but are not limited to, *M. aminovorans, M. chloromethanicum, M. dichloromethanicum, M. extorquens, M. fujisawaense, M. mesophilicum, M. organophilum, M. radiotolerans, M rhodesianum, M. rhodinum, M. thiocyanatum, M. nodulans, M. cerastii, M. gossipiicola, Methylobacterium* sp. strain LMG6378, *M. phyllosphaerae, M. oryzae, M. platani, M. populi*, and *M. zatmanii*. In certain embodiments, monocultures or co-cultures of *Methylobacterium* and resultant fermentation broths and fermentation broth products provided herein can consist of one or more *Methylobacterium*. However, the methods provided herein can also be used on other *Methylobacterium*. *Methylobacterium* can also be obtained by various published methods (Madhaiyan et al., 2007). In certain embodiments, such other *Methylobacterium* that can be used will be *Methylobacterium* having 16S RNA sequences of at least about 60%, 70%, 80%, 90%, or 95% sequence identity to the 16S RNA sequences of other known *Methylobacterium*. Typing of *Methylobacterium* by use of 16S RNA sequence comparisons is at least described by Cao et al, 2011. In certain embodiments, the mono-cultures or co-cultures and resultant products can comprise a *Methylobacterium* that can colonize plants and/or plant parts. *Methylobacterium* that can colonize plants and/or plant parts include, but are not limited to, *M. extorquens, M. nodulans*, and *M. mesophilicum*. *Methylobacterium* that can colonize plants and/or plant parts also include, but are not limited to, *Methylobacterium cerastii* species (with a representative strain available as DSM 23679 from the Leibniz Institute DSMZ-German Collection of Microorganisms and Cell Cultures ("DSMZ"), Braunschweig, Germany), *Methylobacterium gossipiicola* species (with a representative strain available as NRRL B-51692 from the USDA ARS, Peoria, Ill., USA), *Methylobacterium* sp. strain LMG6378 (available from the Belgian Co-ordinated Collection of Micro-organisms/Laboratorium voor Microbiologie ("BCCLM") Ghent, Belgium), *Methylobacterium phyllosphaerae* species (with a representative strain available as available as DSM 19779T from the DSMZ), *Methylobacterium oryzae* species (with a representative strain available as DSM 18207T from the DSMZ), *Methylobacterium nodulans* species (with a representative strain available as LMG 21967 from the BCCLM), *Methylobacterium platani* species (with a representative strain available as KCTC 12901 from the Korean Collection for Type Cultures, Yusong-Ku, Taejon, KR ("KCTC"), and *Methylobacterium populi* species (with a representative strain available as ATCC BAA-705 from the ATCC). Fermentation broths, fermentation broth products, compositions, methods of making the same, and methods of using the same, including, but not limited to, methods of treating plants, where the *Methylobacterium* is a *Methylobacterium* that can colonize a plant and/or a plant part that is selected from the group consisting of *M. extorquens, M. nodulans, M mesophilicum, M. cerastii, M. gossipiicola, Methylobacterium* sp. strain LMG6378, *M. phyllosphaerae, M. oryzae, M. platani*, and *M. populi* are thus provided. Methods of isolating other *Methylobacterium* that can colonize plants and/or plant parts have been described in various publications and can also be used (see Madhaiyan et al., and references cited therein). Without seeking to be limited by theory, it is believed that the methods of culturing *Methylobacterium* in a biphasic media comprising a liquid and a solid substance provided herein can be especially advantageous for growing *Methylobacterium* that can colonize plants and/or plant parts or that were isolated from the surfaces of plants and/or plant parts.

Representative *Methylobacterium* that can be used in the fermentation broths, fermentation broth products, compositions and related methods provided herein include, but are not limited to, the *Methylobacterium* of Table 1.

TABLE 1

Representative *Methylobacterium*

| *Methylobacterium* | Depository Accession Numbers for Type Strain |
|---|---|
| *Methylobacterium adhaesivum* | AR27 = CCM 7305 = CECT 7069 = DSM 17169T = KCTC 22099T |
| *Methylobacterium aerolatum* | DSM 19013 = JCM 16406 = KACC 11766 |
| *Methylobacterium aminovorans* | ATCC 51358 = CIP 105328 = IFO (now NBRC) 15686 = JCM 8240 = VKM B-2145 |
| *Methylobacterium aquaticum* | CCM 7218 = CECT 5998 = CIP 108333 = DSM 16371 |
| *Methylobacterium brachiatum* | DSM 19569 = NBRC 103629 = NCIMB 14379 |
| *Methylobacterium bullatum* | DSM 21893 = LMG 24788 |
| *Methylobacterium cerastii* | CCM 7788 = CCUG 60040 = DSM 23679 |

TABLE 1-continued

Representative *Methylobacterium*

| *Methylobacterium* | Depository Accession Numbers for Type Strain |
|---|---|
| *Methylobacterium chloromethanicum* | NCIMB 13688 = VKM B-2223 |
| *Methylobacterium dichloromethanicum* | CIP 106787 = DSM 6343 = VKM B-2191 |
| *Methylobacterium extorquens* | ATCC 43645 = CCUG 2084 = DSM 1337 = IAM 12631 = IFO (now NBRC) 15687 = JCM 2802 = NCCB 78015 = NCIB (now NCIMB) 9399 = VKM B-2064. |
| *Methylobacterium fujisawaense* | ATCC 43884 = CIP 103775 = DSM 5686 = IFO (now NBRC) 15843 = JCM 10890 = NCIB (now NCIMB) 12417 |
| *Methylobacterium gossipiicola* | CCM 7572 = NRRL B-51692 |
| *Methylobacterium gregans* | DSM 19564 = NBRC 103626 = NCIMB 14376 |
| *Methylobacterium hispanicum* | GP34 = CCM 7219 = CECT 5997 = CIP 108332 = DSM 16372 |
| *Methylobacterium iners* | DSM 19015 = JCM 16407 = KACC 11765 |
| *Methylobacterium isbiliense* | CCM 7304 = CECT 7068 |
| *Methylobacterium jeotgali* | KCTC 12671 = LMG 23639 |
| *Methylobacterium komagatae* | DSM 19563 = NBRC 103627 = NCIMB 14377 |
| *Methylobacterium longum* | CECT 7806 = DSM 23933 |
| *Methylobacterium lusitanum* | DSM 14457 = NCIMB 13779 = VKM B-2239 |
| *Methylobacterium marchantiae* | CCUG 56108 = DSM 21328 |
| *Methylobacterium mesophilicum* | ATCC 29983 = CCUG 16482 = CIP 101129 = DSM 1708 = ICPB 4095 = IFO (now NBRC) 15688 = JCM 2829 = LMG 5275 = NCIB (now NCIMB) 11561 = NRRL B-14246 |
| *Methylobacterium nodulans* | LMG 21967 = ORS 2060 |
| *Methylobacterium organophilum* | ATCC 27886 = CIP 101049 = DSM 760 = HAMBI 2263 = IFO (now NBRC) 15689 = JCM 2833 = LMG 6083 = NCCB 78041 = VKM B-2066 |
| *Methylobacterium oryzae* | DSM 18207 = JCM 16405 = KACC 11585 = LMG 23582 |
| *Methylobacterium persicinum* | DSM 19562 = NBRC 103628 = NCIMB 14378 |
| *Methylobacterium phyllosphaerae* | DSM 19779 = JCM 16408 = KACC 11716 = LMG 24361 |
| *Methylobacterium platani* | JCM 14648 = KCTC 12901 |
| *Methylobacterium podarium* | ATCC BAA-547 = DSM 15083 |
| *Methylobacterium populi* | ATCC BAA-705 = NCIMB 13946 |
| *Methylobacterium radiotolerans* | ATCC 27329 = CIP 101128 = DSM 1819 = IFO (now NBRC) 15690 = JCM 2831 = LMG 2269 = NCIB (now NCIMB) 10815 = VKM B-2144 |
| *Methylobacterium rhodinum* | ATCC 14821 = CIP 101127 = DSM 2163 = IFO (now NBRC) 15691 = JCM 2811 = LMG 2275 = NCIB (now NCIMB) 9421 = VKM B-2065 |
| *Methylobacterium suomiense* | DSM 14458 = NCIMB 13778 = VKM B-2238 |
| *Methylobacterium tardum* | DSM 19566 = NBRC 103632 = NCIMB 14380 |
| *Methylobacterium thiocyanatum* | ATCC 700647 = DSM 11490 = JCM 10893 = VKM B-2197 |
| *Methylobacterium variabile* | CCM 7281 = CECT 7045 = DSM 16961 |
| *Methylobacterium zatmanii* | ATCC 43883 = CCUG 36916 = CIP 103774 = DSM 5688 = IFO (now NBRC) 15845 = JCM 10892 = LMG 6087 = NCIB (now NCIMB) 12243 = VKM B-2161 |

Depository Key
ATCC: American Type Tissue Culture Collection, Manassas, VA, USA
CCUG: Culture Collection, University of Göteborg, Sweden
CIP: Collection de l'Institut Pasteur, Paris, FR
DSM: DSMZ-German Collection of Microorganisms and Cell Cultures ("DSMZ"), Braunschweig, Germany
JCM: Japan Collection of Microorganisms, Saitama, Japan
LMG: Belgian Co-ordinated Collection of Micro-organisms/Laboratorium voor Microbiologie ("BCCLM") Ghent, Belgium
NBRC: Biological Resource Center (NBRC), Chiba, Japan
NCIMB: National Collections of Industrial, Food and Marine Bacteria, UK
NRRL: USDA ARS, Peoria, IL., USA In certain embodiments, the mono-cultures or co-cultures and resultant fermentation broths and fermentation broth products can comprise one or more *Methylobacterium* isolates or mutants that produce increased levels of useful nutrients or plant growth regulators. U.S. Pat. No. 8,153,118 discloses various *Methylobacterium* isolates that produce increased levels of vitamin B-12 and amino acids that can be used in the methods and compositions provided herein. Fermentation broths, fermentation broth products, and compositions that comprise one or more of the *Methylobacterium* such as *Methylobacterium* mutant B12-11 having American Tissue Type Collection accession number ATCC PTA-1561 that overproduces vitamin B-12, *Methylobacterium rhodinum* (ATCC #43282) that over-produces the amino acid threonine, *Methylobacterium* sp. (ATCC #21371) that over-produces the amino acid L-glutamic acid, *Methylobacterium* sp. (ATCC #21372) that over-produces the amino acid L-glutamic acid, *Methylobacterium* sp. (ATCC #21926) over-produces the amino acid L-lysine, *Methylobacterium* sp. (ATCC #21969) over-produces the amino acid L-glutamic acid, *Methylobacterium* sp. (ATCC #21927) over-produces the amino acids L-lysine, L-aspartic acid, L-alanine, L-valine, L-leucine, and L-arginine, and/or *Methylobacterium* sp. (ATCC #21438) that produces single-cell protein are also provided.

In certain embodiments, the fermentation broth, fermentation broth product, or compositions provided herein can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma virens,* and *Streptomyces lydicus* strains. Other microorganisms that are added can be genetically engineered or naturally occurring isolates that are available as pure cultures. In certain embodiments, it is anticipated that the bacterial or fungal microorganism can be provided in the fermentation broth, fermentation broth product, or composition in the form of a spore. Still other microorganisms that can be added include, but are not limited to, microorganisms that are photosynthetic microorganisms. Such photosynthetic organisms include, but are not limited to, algae. Such algae can include, but are not limited to, algae of the genii of *Protococcus, Ulva, Codium, Enteromorpha, Neochloris,* and/or *Chlamydomonas*.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Exemplary liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria—Bertani Broth").

In general, the solid substance used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to *Methylobacterium* when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include natural substances of animal, plant, microbial, fungal, or mineral origin, manmade substances, or combinations of natural and manmade substances. In certain embodiments, the solid substances are inanimate solid substances. Inanimate solid substances of animal, plant, microbial, or fungal origin can be obtained from animals, plants, microbes, or fungi that are inviable (i.e. no longer living) or that have been rendered inviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii, Chlorella, Dunaliella tertiolecta, Gracilaria, Pleurochrysis carterae, Sargassum,* and *Ulva*. In still other embodiments, the solid substance can be an inactivated (i.e. inviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, bark, seeds, and combinations thereof. Products obtained from processed plant parts including but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance can be a solid substance that provides for adherent growth of the *Methylobacterium* on the solid substance. *Methylobacterium* that are adhered to a solid substance are *Methylobacterium* that cannot be substantially removed by simply washing the solid substance with the adherent *Methylobacterium* with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, by not limited to, decanting liquid from a washed solid phase or passing liquid through a solid phase on a filter that permits flow through of bacteria in the liquid. In certain embodiments, the adherent *Methylobacterium* that are associated with the solid can include both *Methylobacterium* that are directly attached to the solid and/or *Methylobacterium* that are indirectly attached to the solid substance.

*Methylobacterium* that are indirectly attached to the solid substance include, but are not limited to, *Methylobacterium* that are attached to another *Methylobacterium* or to another microorganism that is attached to the solid substance, *Meth-* ylobacterium that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Biphasic culture methods provided can yield fermentation broths with *Methylobacterium* at a titer of greater than about $5 \times 10$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter. In certain embodiments, fermentation broths provided herein can comprise *Methylobacterium* at a titer of at least about $5 \times 10^8$ colony-forming units per milliliter to at least about $3 \times 10^{10}$ colony-forming units per milliliter, at least about $5 \times 10^1$ colony-forming units per milliliter to at least about $4 \times 10^{10}$ colony-forming units per milliliter, or at least about $5 \times 10^1$ colony-forming units per milliliter to at least about $6 \times 10^{10}$ colony-forming units per milliliter. In certain embodiments, fermentation broths provided herein can comprise *Methylobacterium* at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation broths provided herein will comprise *Methylobacterium* at a titer of at least about $1 \times 10^{10}$ colony-forming units per milliliter to at least about $3 \times 10^{10}$ colony-forming units per milliliter, at least about $1 \times 10^{10}$ colony-forming units per milliliter to at least about $4 \times 10^{10}$ colony-forming units per milliliter, or at least about $1 \times 10^{10}$ colony-forming units per milliliter to at least about $6 \times 10^{10}$ colony-forming units per milliliter. In certain embodiments, fermentation broths provided herein will comprise *Methylobacterium* at a titer of, at least about $3 \times 10^{10}$ colony-forming units per milliliter to at least about $4 \times 10^{10}$ colony-forming units per milliliter, or at least about $3 \times 10^{10}$ colony-forming units per milliliter to at least about $6 \times 10^{10}$ colony-forming units per milliliter.

Also provided herein are methods for obtaining a *Methylobacterium* preparation where the *Methylobacterium* either are grown in a culture vessel that comprises or contains one or more solid surfaces that provide for adherent growth of the *Methylobacterium* or are grown in media that comprises a liquid phase and a solid phase, and then harvested by removal from the solid surface or the solid phase to which they have adhered. In certain embodiments where a solid surface that provides for adherent growth of the *Methylobacterium* is used, the solid surface can form part of the culture vessel itself. In still other embodiments, a solid surface that is contained in a culture vessel is a solid surface that can be detached from the culture vessel, particularly after or during the course of a fermentation run, to facilitate removal of the adherent *Methylobacterium*. Exemplary and non-limiting solid surfaces include beads, rings, cylinder and other shapes that provide for improved surface area to volume ratios. Solid surfaces used in the culture vessel can be either porous or smooth. Exemplary solid surfaces used culture vessels can be made from materials that include, but are not limited to, coated or uncoated metals, glass, plastics, ceramics, or combinations thereof that permit adherent growth of *Methylobacterium*. Following the culturing, *Methylobacterium* that have adhered to the solid surface or the solid phase can be harvested by one or more of a physical and/or chemical treatment(s). In certain embodiments of these methods, non-adherent *Methylobacterium* that have accumulated in the liquid phase can also be harvested. Chemical treatments used to harvest the *Methylobacterium* include, but are not limited to, exposing the adherent *Methylobacterium* to a shift in ionic strength, a shift in pH, a detergent treatment, a solvent treatment, an enzymatic treatment, and combinations thereof. Enzymatic treatments used to harvest the *Methylobacterium* can include, but are not limited to, exposing *Methylobacterium* adhered to the solid surface or to the solid phase to a protease, a lipase, a glucanase, or any combination thereof. Detergent treatments used to harvest the *Methylobacterium* can include, but are not limited to, exposing *Methylobacterium* adhered to the solid surface or the solid phase to an ionic detergent, a non-ionic detergent, or any combination thereof. Physical treatments used to harvest the *Methylobacterium* can include, but are not limited to, exposing *Methylobacterium* adhered to the solid surface or to the solid phase to sonication, scraping, a pressurized liquid, a pressurized slurry, heat, or any combination thereof. In certain embodiments, non-adherent *Methylobacterium* can be harvested from the liquid in the culture vessel. In still other embodiments, non-adherent *Methylobacterium* can be harvested from the liquid in the culture vessel and adherent *Methylobacterium* harvested from the solid surface.

Without seeking to be limited by theory, it is believed that the solid in the biphasic culture media provides a surface on which *Methylobacterium* can adhere to and grow upon. Such adherent growth on the solid in the biphasic culture media is believed to be more rapid (i.e. provide for a decreased doubling time) than growth in the absence of the solid. It is believed that both the number (i.e. colony forming units per milliliter) and density (*Methylobacterium* per square micrometers) of *Methylobacterium* will increase during the course of the fermentation until a maximum number and/or density is reached. In certain embodiments, it is believed that daughter cells from an adherent mother cell can either grow on the solid surface, grow on the adherent mother cell, and/or be shed into the liquid phase. It is also thus believed that the number (i.e. colony forming units per milliliter) of *Methylobacterium* in the liquid phase can increase until a maximum number is reached.

Solid substances with adherent *Methylobacterium* can be used to make various compositions useful for treating plants or plant parts. Alternatively, fermentation broths or fermentation broth products comprising solid substances with adherent *Methylobacterium* can be used to treat plants or plant parts. Plants, plant parts, and, in particular, plant seeds that have been at least partially coated with the fermentation broth products or compositions are thus provided. Also provided are processed plant products that contain the fermentation broth products or compositions. Solid substances with adherent *Methylobacterium* can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent *Methylobacterium* that can be readily identified by comparing a treated and an untreated plant, plant part, plant seed, or processed product thereof.

Fermentation broths, fermentation broth products, fermentation products, or other compositions comprising solid substances with adherent *Methylobacterium* can be used to produce industrial products or recombinant proteins or in bioremediation.

Compositions useful for treating plants or plant parts that comprise the solid substance with adherent *Methylobacterium* can also comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), an emulsion, or a suspension.

Agriculturally acceptable adjuvants used in the compositions include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions are also provided herein. Treated plants, and treated plant parts obtained therefrom, include, but are not limited to, corn, *Brassica* sp. (e.g., *B. napus, B. rapa, B. juncea*), alfalfa, rice, rye, sorghum, millet (e.g., pearl millet (*Pennisetum glaucum*), proso millet (*Panicum miliaceum*), foxtail millet (*Setaria italica*), finger millet (*Eleusine coracana*)), sunflower, safflower, soybean, tobacco, potato, peanuts, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, oats, barley, tomatoes lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Conifer plants and plant parts that can be treated include, but are not limited to, pines such as loblolly pine, slash pine, ponderosa pine, lodgepole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* adhered thereto are also provided herein. Also provided herein are processed plant products that comprise a solid substance with *Methylobacterium* adhered thereto.

In certain embodiments, seeds are treated by exposing the seeds to the fermentation broths, fermentation broth products, fermentation products, and compositions provided herein. Seeds can be treated with the fermentation broths, fermentation broth products, and compositions provided herein by methods including, but not limited to, imbibition, coating, spraying, and the like. Seed treatments can be effected with both continuous and/or a batch seed treaters. In certain embodiments, the coated seeds may be prepared by slurrying seeds with a coating composition containing a fermentation broth, fermentation broth product, or compositions provided that comprise the solid substance with *Methylobacterium* and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* includes, but is not limited to, a range of 0.1 to 25% by weight of the seed, 0.5 to 5% by weight of the seed, and 0.5 to 2.5% by weight of seed. In certain embodiments, a solid substance used in the seed coating or treatment will have *Methylobacterium* adhered thereon. In certain embodiments, a solid substance used in the seed coating or treatment will be associated with *Methylobacterium* and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

Use of the fermentation broths, fermentation broth products, and compositions provided herein to promote nodal root formation in cereal plants is also provided herein. Early development of a vigorous nodal root system is important in establishing stands of cereal plant crops that include, but are not limited to, corn, barley, millet, oat, rice, rye, sorghum, triticale, and wheat. The first roots that emerge from a cereal plant seed (the radicle and seminal roots) function mainly in the uptake of water from the soil. The radicle seminal roots do not provide other nourishment, which early in the growth of the seedling is provided by energy and nutrient reserves in the kernel. When nodal roots emerge from the cereal plant stem, growth of the seminal roots slows dramatically and they contribute little to the season-long maintenance of the cereal plant. Instead, the nodal root system plays this role. Thus, the early and vigorous establishment of a nodal root system plays a key role in the development of a uniform stand of a cereal plant crop. Failure to do so results in stunted plants and other deficiencies that end in lower yields at harvest.

Provided herein are fermentation broths, fermentation broth products, and compositions that increase nodal root growth in cereal plants relative to untreated cereal plants that have not been exposed to the fermentation broths, fermentation broth products, and compositions. In certain embodiments, cereal plant parts, including, but not limited to, a seed, a leaf, or a coleoptile can be treated with the fermentation broths, fermentation broth products, and compositions to increase cereal plant nodal root growth. Treatments or applications can include, but are not limited to, spraying, coating, partially coating, immersing, and/or imbibing the cereal plant or cereal plant parts with the fermentation broths, fermentation broth products, and compositions provided herein. In certain embodiments, seeds can be immersed and/or imbibed with a fermentation broth, with a fermentation broth product that has been partially or completely resuspended in a liquid, or with a liquid, semi-liquid, or slurry of a composition provided herein. Such seed immersion or imbibition can be sufficient to provide for an increase in nodal root growth in a cereal plant in comparison to nodal root growth in a mock or untreated cereal plant. Such increases in nodal root growth include increases in the numbers, length, dry weight, and/or wet weight of the nodal roots in treated cereal plants relative to untreated cereal plants. In certain embodiments, cereal plant seeds can be immersed and/or imbibed for at least 1, 2, 3, 4, 5, or 6 hours. Such immersion and/or imbibition can, in certain embodiments, be conducted at temperatures that are not deleterious to the cereal plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Amounts of the fermentation broths, fermentation broth products, and compositions sufficient to provide for an increase in nodal root growth in a cereal plant can thus be determined by measuring any or all of an increase in the number, length, dry weight, and/or wet weight of the nodal roots in treated cereal plants relative to untreated cereal plants. In certain embodiments, an amount of a fermentation broth provided herein that is sufficient to provide for an increase in nodal root growth in a cereal plant can be a fermentation broth with *Methylobacterium* at a titer of at least about $5 \times 10^1$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a fermentation broth provided herein that is sufficient to provide for an increase in nodal root growth in a cereal plant can be a fermentation broth with *Methylobacterium* at a titer of about $5 \times 10^1$ colony-forming units per milliliter to at least about $6 \times 10^{10}$ colony-forming units per milliliter. In certain embodiments, an amount of a fermentation broth product provided herein that is sufficient to provide for an increase in nodal root growth in a cereal plant can be a fermentation broth product with a *Methylobacterium* titer of the solid phase of that product is at least about $5 \times 10^8$ colony-forming units per gram to at least about $6 \times 10^{10}$ colony-forming units of *Methylobacterium* per gram of the solid phase. In certain embodiments, an amount of a composition provided herein that is sufficient to provide for an increase in nodal root growth in a cereal plant can be a composition with a *Methylobacterium* titer of at least about $5 \times 10^8$ colony-forming units per gram to at least about $6 \times 10^{10}$ colony-forming units of *Methylobacterium* per gram of particles in the composition containing the particles that comprise a solid substance wherein a mono-culture or co-culture of *Methylobacterium* is adhered thereto.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific embodiments that are disclosed, while still obtaining like or similar results, without departing from the scope of the invention.

Example 1. Growth of PPFM Bacteria on Solid Agar Plate Media

For the growth of PPFM bacteria on solid agar plate media, a variety of standard media were tested.

One medium used was ammonium mineral salts (AMS) medium (Whittenbury et al., 1970). AMS medium contains, per liter, 700 milligrams of dibasic potassium phosphate anhydrous, 540 milligrams of monobasic potassium phosphate anhydrous, one gram of magnesium sulfate heptahydrate, 500 milligrams of ammonium chloride anhydrous, 200 milligrams of calcium chloride dehydrate, 4 milligrams of ferric sulfate heptahydrate, 100 micrograms of zinc sulfate heptahydrate, 30 micrograms of manganese chloride tetrahydrate, 300 micrograms of boric acid anhydrous, 200 micrograms of cobalt chloride hexahydrate, 10 micrograms of copper chloride dehydrate, 20 micrograms of nickel chloride hexahydrate, and 60 micrograms of sodium molybdate dehydrate.

AMS medium was prepared from four stock solutions, listed below

| Stock solution I: for one liter at 50X concentration | |
|---|---|
| dibasic potassium phosphate, anhydrous | 35 grams |
| monobasic potassium phosphate, anhydrous | 27 grams |

| Stock solution II: for one liter at 50X concentration | |
|---|---|
| magnesium sulfate heptahydrate | 50 grams |
| ammonium chloride, anhydrous | 25 grams |

| Stock soultion III: for one liter at 50X concentration | |
|---|---|
| calcium chloride dihydrate | 10 grams |

| Trace metals stock solution: for one liter at 1000X concentration | |
|---|---|
| ferric sulfate heptahydrate | 4 grams |
| zinc sulfate heptahydrate | 100 milligrams |
| manganese chloride tetrahydrate | 30 milligrams |
| boric acid, anhydrous | 300 milligrams |
| cobalt chloride hexahydrate | 200 milligrams |
| copper chloride dihydrate | 10 milligrams |
| nickel chloride hexahydrate | 20 milligrams |
| sodium molybdate dihydrate | 60 milligrams |

Stock solutions I, II, and III were autoclaved separately. The trace metals stock solution could not be autoclaved, as most of the salts precipitated out during the autoclaving step, and so it was filter-sterilized through a 0.2 micrometer filter apparatus. These steps were necessary to insure the preparation of a water-clear AIS culture medium with all ingredients in solution. As originally described by Whittenbury et al. (1970), the phosphate-containing components of the AMS medium were segregated from the other components until the final finishing steps of the medium preparation, preventing the formation of insoluble magnesium phosphate and calcium phosphate crystals.

To prepare one liter of solid agar plate media with an AIS base, 15 grams of agar were added to 940 ml of distilled water, and this mixture was autoclaved. After autoclaving, 20 ml each of stock solutions I, II, and III were added, along with one ml of the filter-sterilized trace metals stock solution.

If other medium components, such as a carbon source, were to be incorporated, for the most part these were added to the water and agar mixture before autoclaving. The one exception to this was methanol, which was filter-sterilized through a 0.2 micrometer filter apparatus and added after the base medium had been autoclaved.

A second medium used was Vogel-Bonner (VB) minimal culture medium (Vogel and Bonner, 1956). VB medium contains, per liter, 298 milligrams of magnesium sulfate heptahydrate, 14.93 grams of anhydrous dibasic potassium phosphate, 5.22 grams of sodium ammonium phosphate tetrahydrate, and 2.73 grams of anhydrous citric acid (the free acid form).

Vogel-Bonner minimal medium was prepared from a 25× stock solution of the salts and citric acid. This 25× stock solution was prepared by dissolving in one liter of distilled water the following amounts of each ingredient, in the order listed, and making sure each one was completely dissolved before adding the next one: 7.46 grams of magnesium sulfate heptahydrate, 68.23 grams of anhydrous citric acid, 373.13 grams of anhydrous dibasic potassium phosphate, and 130.60 grams of sodium ammonium phosphate tetrahydrate. By first dissolving the magnesium sulfate and then adding the citric acid, the magnesium ions were chelated by the citrate ions, preventing the formation of insoluble magnesium phosphate crystals when the phosphate salts are added. This insured the preparation of a water-clear culture medium with all ingredients in solution.

To prepare one liter of solid agar plate media with a VB base, 15 grams of agar were added to 960 ml of distilled water and this mixture was autoclaved. After autoclaving, 40 ml of the 25× VB salts stock solution were added.

If other medium components, such as a carbon source, were to be incorporated, for the most part these were added to the water and agar mixture before autoclaving. The one exception to this was methanol, which was filter-sterilized through a 0.2 micrometer filter apparatus and added after the base medium had been autoclaved.

A third medium used was LB broth. LB broth contains, per liter, 10 grams of tryptone, 5 grams of yeast extract, and 10 grams of sodium chloride. All components were dissolved in one liter of distilled water and autoclaved. This medium was water-clear, with all ingredients in solution.

To prepare one liter of solid agar plate media with an LB base, 15 grams of agar were added to one liter of LB broth, and this mixture was autoclaved.

Corpe and Basile (1982) conducted a systematic survey of the growth of various strains of PPFM bacteria in AMS media containing various carbon sources. Many of the tested substances supported little to no growth of PPFM bacteria. Corpe and Basile reported that glycerol and glutamate were relatively good carbon sources for PPFM bacteria, and that methanol, glucose, aspartate, succinate and malate were intermediate as carbon sources for PPFM bacteria.

The Applicants measured the growth of *Methylobacterium extorquens* on LB plates, as well as on AMS and VB plates supplemented with various carbon sources. The carbon sources, listed below, were all added to the AMS or VB base salts media at 10 grams per liter. In addition, some media compositions were tested that included peptone at 10 grams per liter. The *Methylobacterium extorquens* was streaked out on the various agar plates, and they were incubated at 30 degrees C. for up to two weeks. Growth was measured as the number of days of incubation required for the colonies to become full-sized (about 2 millimeters in diameter); for those growth conditions where full-sized colonies did not form even after prolonged incubation, the colonies were scored as medium-sized (about 1 millimeters in diameter) or small-sized (about 0.5 millimeters in diameter or smaller). All of the colonies observed were of a deep, saturated pink color, as is characteristic of PPFM bacteria.

The results were as follows:

| | |
|---|---|
| VB plus aspartate | small-sized in 9 days |
| VB plus succinate | small-sized in 10 days |
| VB plus malate | small-sized in 10 days |
| LB | full-sized in 9 days |
| AMS plus glucose | full-sized in 9 days |
| VB plus glucose | full-sized in 14 days |
| AMS plus methanol | full-sized in 6 days |
| VB plus methanol | medium-sized in 10 days |
| AMS plus glutamate and peptone | full-sized in 5 days |
| AMS plus glycerol and peptone | full-sized in 5 days |
| VB plus glycerol and peptone | full-sized in 6 days |

The fastest and most abundant growth of the PPFM bacterium *Methylobacterium extorquens* on the tested solid agar plate media was on AIS plus glycerol and peptone or AMS plus glutamate and peptone, followed closely by AMS plus methanol or VB plus glycerol and peptone. Growth on the other tested media was significantly slower.

Example 2. Growth of PPFM Bacteria in Clear, Monophasic Liquid Media

For those four solid agar plate media found in Example 1 to have supported the fastest and most abundant growth of the PPFM bacterium *Methylobacterium extorquens*, the corresponding liquid versions (that is, no added agar) were prepared and tested. These four liquid media, prepared as described in Example 1 (with the sole exception being that they did not contain any agar) were all water-clear liquids, with all ingredients in solution.

To flasks containing 100 milliliters of these four liquid media, an inoculum of the PPFM bacterium *Methylobacterium extorquens* was added to give an initial titer of about $1 \times 10^5$ colony-forming units (CFU) per milliliter. The flasks were placed on a rotary shaker incubator set and grown for 5 days at 30 degrees C. and 250 rpm. At the end of the 5 days of incubation, the titers of PPFM bacteria in the flasks were determined. The results were:

| liquid medium | initial titer of PPFM | titer of PPFM after 5 days |
|---|---|---|
| AMS plus glycerol and peptone | $1.4 \times 10^5$ | $4.5 \times 10^5$ |
| AMS plus glutamate and peptone | $2.0 \times 10^5$ | $3.8 \times 10^5$ |
| AMS plus methanol | $1.1 \times 10^5$ | $2.1 \times 10^5$ |
| VB plus glycerol and peptone | $1.7 \times 10^5$ | $1.3 \times 10^5$ |

A striking aspect of these results is the very poor growth of the PPFM bacteria in all of these water-clear liquid media, in the presence of the exact same nutrients as were present in the solid agar plate forms of these media on which the PPFM bacteria grew rapidly and abundantly (as described in Example 1). Indeed, in all of these flasks, there was little or no visible turbidity (the classical indication of microbial growth) and no hint of a pink hue whatsoever.

Example 3. Growth of PPFM Bacteria in a Biphasic Culture Media Containing Insoluble Salt Crystals For the preparation of the biphasic culture media, liquid AMS plus glycerol and peptone medium was made turbid (i.e. provided with a solid substance) by deliberately forming insoluble crystals of magnesium phosphate and/or calcium phosphate. To deliberately form insoluble crystals in the media, the preparation method described in Example 1 was altered as follows. All components except the trace metals stock solution were mixed together before autoclaving. That is, to 940 ml of distilled water were added 20 ml each of stock solutions I, II, and III, along with 10 grams of glycerol and 10 grams of peptone. After autoclaving, the medium was completed by the addition of one ml of filter-sterilized trace metals stock solution. The autoclaving of the components of stock solutions I, II, and III, mixed together before autoclaving, resulted in the formation of insoluble salt crystals, presumably primarily magnesium phosphate dibasic and/or calcium phosphate dibasic. After autoclaving, the AMS plus glycerol and peptone medium made by this preparation method yielded a liquid medium that was very turbid with these salt crystals. This new liquid medium was designated "turbid AMS plus glycerol and peptone".

To a flask containing 100 milliliters of the turbid AMS plus glycerol and peptone, an inoculum of the PPFM bacterium *Methylobacterium extorquens* was added to give an initial titer of about $1\times10^5$ colony-forming units (CFU) per milliliter. The flask was placed on a rotary shaker incubator set and grown for 3 days at 30 degrees C. and 250 rpm. After just two days, the flask had developed a deep, saturated pink turbidity, indicating fast and abundant growth of PPFM bacteria. At both 2 days and 3 days after inoculation, the titers of PPFM bacteria in the flask were determined. The results were:

| liquid medium | initial titer of PPFM | titer of PPFM after 2 days | titer of PPFM after 3 days |
| --- | --- | --- | --- |
| turbid AMS plus glycerol and peptone | $1.7 \times 10^5$ | $1.3 \times 10^8$ | $1.7 \times 10^9$ |

Two striking aspects of this result were the very fast growth of the PPFM bacteria, and their growth to titers approaching 10,000-fold higher than achieved in clear AMS plus glycerol and peptone liquid medium (as shown in Example 2).

Example 4. Growth of PPFM Bacteria in Liquid Media Containing Agar

For the preparation of solid agar plate media, agar is typically added at about 15 grams per liter of medium. To test whether lower amounts of agar, at levels too low to gel or solidify the medium, would be effective at promoting the fast and abundant growth of PPFM bacteria, small amounts of agar were added to AMS plus glycerol and peptone liquid medium.

This liquid medium was prepared as described in Example 1, that is, by the preparation method designed to prevent the formation of insoluble salt crystals of magnesium phosphate and calcium phosphate. The agar, as described in Example 1, was added to the water before autoclaving. The amounts of agar tested were, per liter, 750 milligrams, 1.5 grams, and 3 grams. These new liquid media were designated "AMS plus glycerol and peptone and agar".

To flasks containing 100 milliliters of the AMS plus glycerol and peptone and agar, an inoculum of the PPFM bacterium *Methylobacterium extorquens* was added to give an initial titer of about $1\times10^5$ colony-forming units (CFU) per milliliter. The flasks were placed on a rotary shaker incubator set and grown for 3 days at 30 degrees C. and 250 rpm. After just two days, the flasks had all developed a deep, saturated pink turbidity, indicating fast and abundant growth of PPFM bacteria. At both 2 days and 3 days after inoculation, the titers of PPFM bacteria in the flasks were determined. The results were:

| liquid medium | initial titer of PPFM | titer of PPFM after 2 days | titer of PPFM after 3 days |
| --- | --- | --- | --- |
| AMS plus glycerol and peptone and 750 mg agar | $1.3 \times 10^5$ | $6.4 \times 10^7$ | $8.0 \times 10^7$ |
| AMS plus glycerol and peptone and 1.5 grams agar | $1.3 \times 10^5$ | $3.1 \times 10^7$ | $2.0 \times 10^8$ |
| AMS plus glycerol and peptone and 3 grams agar | $1.2 \times 10^5$ | $1.8 \times 10^8$ | $5.1 \times 10^8$ |

Two striking aspects of this result are the very fast growth of the PPFM bacteria, and their growth to titers approaching 1000-fold higher than achieved in clear AMS plus glycerol and peptone liquid medium (as shown in Example 2). The data acquired after 3 days of growth also indicate that increased amounts of growth are correlated to increased amounts of agar.

Example 5. Growth of PPFM Bacteria in Liquid Media Containing Diatomaceous Earth To test whether diatomaceous earth would be effective at promoting the fast and abundant growth of PPFM bacteria, small amounts of diatomaceous earth were added to AMS plus glycerol and peptone liquid medium. This liquid medium was prepared as described in Example 1, that is, by the preparation method designed to prevent the formation of insoluble salt crystals of magnesium phosphate and calcium phosphate. The diatomaceous earth was added to the water before autoclaving. The amounts of diatomaceous tested were, per liter, 500 milligrams, 1 gram, 1.5 grams, and 2 grams. These new liquid media were designated "AMS plus glycerol and peptone and diatomaceous earth".

To flasks containing 100 milliliters of the AMS plus glycerol and peptone and diatomaceous earth, an inoculum of the PPFM bacterium *Methylobacterium extorquens* was added to give an initial titer of about $1\times10^5$ colony-forming units (CFU) per milliliter. The flasks were placed on a rotary shaker incubator set and grown for 3 days at 30 degrees C. and 250 rpm. After just two days, the flasks had all developed a deep, saturated pink turbidity, indicating fast and abundant growth of PPFM bacteria. At both 2 days and 3 days after inoculation, the titers of PPFM bacteria in the flasks were determined. The results were:

| liquid medium | initial titer of PPFM | titer of PPFM after 2 days | titer of PPFM after 3 days |
|---|---|---|---|
| AMS plus glycerol and peptone and 500 mg diatomaceous earth | $1.0 \times 10^5$ | $1.8 \times 10^8$ | $1.1 \times 10^9$ |
| AMS plus glycerol and peptone and 1 gram diatomaceous earth | $1.8 \times 10^5$ | $3.0 \times 10^8$ | $8.4 \times 10^8$ |
| AMS plus glycerol and peptone and 1.5 grams diatomaceous earth | $1.4 \times 10^5$ | $4.0 \times 10^8$ | $1.7 \times 10^9$ |
| AMS plus glycerol and peptone and 2 grams diatomaceous earth | $1.7 \times 10^5$ | $3.4 \times 10^8$ | $2.0 \times 10^9$ |

Two striking aspects of this result are the very fast growth of the PPFM bacteria, and their growth to titers approaching 10,000-fold higher than achieved in clear AMS plus glycerol and peptone liquid medium (as shown in Example 2). The data acquired after 2 days of growth also indicate that increased amounts of growth are correlated to increased amounts of agar within the range of 0.5 grams to 1.5 grams per 100 ml of culture.

Example 6. Growth of PPFM Bacteria in a Controlled Bioreactor

The growth of bacteria in flasks, incubated on a rotary shaker, is limited by changes in pH brought about by the metabolism of the carbon source(s) in the growth medium. Controlled bioreactors (also known as "fermenters" or "fermentation vessels") avoid this limitation by maintaining the pH at the desired level through the controlled addition of acids or bases, as appropriate. Another factor which can limit the growth of bacteria is the availability of dissolved oxygen. Controlled bioreactors avoid this limitation by maintaining adequate levels of dissolved oxygen through the controlled adjustment of airflow into the reactor vessel, the agitation rate of the vessel, and the air pressure within the vessel.

When grown in a controlled bioreactor containing the AMS plus glycerol and peptone liquid medium described in Example 1, further supplemented with solid substances such as insoluble salts, agar, or diatomaceous earth as described in Examples 3, 4 and 5, the final titer of PPFM bacteria achieved will be at least 30-fold higher than that achieved in flasks, specifically at least $3 \times 100$ colony-forming units per milliliter.

Example 7. Growth of Various *Methylobacterium* in the Presence and Absence of Various Solids in the Media Various *Methylobacterium* listed in the following Table were obtained from the indicated depository organizations, purified as single colony isolates, and cultured in the presence and absence of solids in AMVS plus glycerol plus peptone media. The solids were sterilized by autoclaving in the media.

TABLE 3

| Depository Accession No. | *Methylobacterium* species |
|---|---|
| DSM-6343 | *Methylobacterium extorquens* |
| DSM-1819 | *Methylobacterium radiotolerans* |
| DSM-13060 | *Methylobacterium extorquens* |
| DSM-18172 | *Methylobacterium organophilum* |

TABLE 3-continued

| Depository Accession No. | *Methylobacterium* species |
|---|---|
| DSM-1708 | *Methylobacterium mesophilicum* |
| DSM-18207 | *Methylobacterium oryzae* |
| DSM-19779 | *Methylobacterium phyllosphaerae* |
| ATCC-14718 | *Methylobacterium extorquens* |
| ATCC-14821 | *Methylobacterium rhodinum* |
| ATCC-21611 | *Methylobacterium rhodesianum* |
| ATCC-35065 | *Methylobacterium fujisawaense* |
| ATCC-43883 | *Methylobacterium zatmanii* |
| ATCC-51358 | *Methylobacterium aminovorans* |
| ATCC-700647 | *Methylobacterium thiocyanatum* |

ATCC: American Type Tissue Culture Collection, Manassas, VA, USA
DSM: DSMZ-German Collection of Microorganisms and Cell Cultures ("DSMZ"), Braunschweig, Germany All of the *Methylobacterium* in the preceding Table grew very poorly or not at all in water-clear AIS plus glycerol plus peptone medium, and all grew very well in the same medium amended (at 2 grams per liter) with one following solids: diatomaceous earth, agar, turbid medium (made so as to be cloudy with insoluble crystals of magnesium phosphate as described in Example 3), bone meal, flax seed meal, "Rare Earth" (a mixture of pyrophyllitic silicate clay and leonardite from General Hydroponics of Sebastopol, Calif., USA), "White Hermit Crab Sand" (a mixture of calcium carbonate and magnesium carbonate from Zoo-Med Laboratories, Inc., of San Luis Obispo, Calif., USA), dried and powdered coconut meat, and crushed egg shell.

Example 8. Photomicroscopy of *Methylobacterium* Grown in the Presence of a Solid in the Media

*Methylobacterium* were purified as single colony isolates and cultured in the presence of diatom shells in liquid growth media. The diatom shells were sterilized by autoclaving in the liquid media prior to inoculation of the thus sterilized media with *Methylobacterium*.

Figure 2:
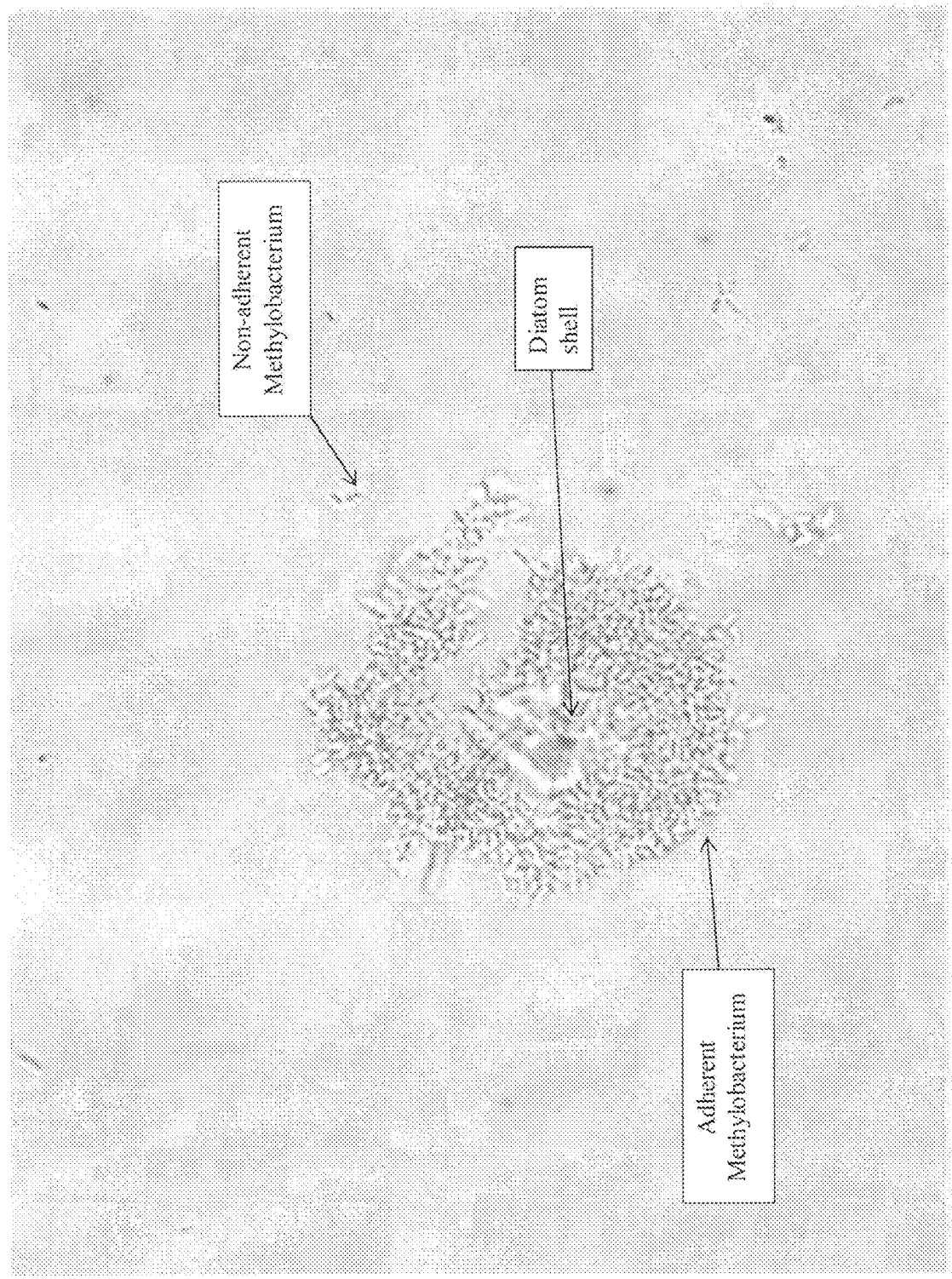
FIG. 2 is a photomicrograph of an aliquot of a fermentation product comprising liquid media, a solid (diatom shells), and *Methylobacterium*. The solid diatom shell, adherent *Methylobacterium*, and non-adherent *Methylobacterium* are indicated by the labels in the photomicrograph. The *Methylobacterium* strain is DSM-6343 *Methylobacterium* extorquens.

The results of the photomicrographic analysis of the cultures are shown in FIGS. 1 and 2. In FIG. 1, some portions of the latticed diatom shell are exposed while other portions of the diatom shell are obscured by the adherent *Methylobacterium* cells. FIG. 1 also shows that there are very few *Methylobacterium* cells in this culture that are not adherent. FIG. 2 shows a diatom shell that is almost completely coated with adherent *Methylobacterium* cells and a few apparently non-adherent *Methylobacterium* cells in the liquid media.

Example 9. Plant Seed or Foliar Treatment Compositions Comprising Solid Substances with Adherent *Methylobacterium*

To obtain compositions suitable for plant seed or foliar treatments, *Methylobacterium* are cultured in liquid media containing a solid substance by any of the methods disclosed or claimed herein, or as described in any of the preceding Examples 3-6. Typically, the *Methylobacterium* are cultured to a high titer (i.e. at least about $5 \times 10^8$ colony-forming units per gram of solid). Adherent *Methylobacterium* associated with the solid are then harvested either with or without any non-adherent *Methylobacterium* present in the culture. Harvesting can be achieved by filtration, centrifugation, decanting, and combinations thereof. Harvested material can be applied directly to seeds or plants in certain instances. In other instances, the harvested material is dried by lyophilization or spray drying and the like prior to application. Dried material can also be reconstituted with liquids as necessary or desired prior to application to plants or seed. In certain cases, the solid materials with the adherent *Methylobacterium* can be disassociated as described herein and either applied directly to the seeds or plants or first dried and then applied to seeds or plants. Solid materials with the adherent *Methylobacterium* can also be first dried, then disassociated as described herein and applied directly to the seeds of plants or used as active ingredients in other compositions for plant or seed treatment. It is also possible to add additional agriculturally acceptable excipients and/or adjuvants to any of the harvested and/or dissociated solid materials with adherent *Methylobacterium*. Added excipients can include woodflours, clays, activated carbon, diatomaceous earth, fine-grain inorganic solids, calcium carbonate and the like. Clays and inorganic solids that can be added as excipients in the compositions include calcium bentonite, kaolin, china clay, talc, perlite, mica, vermiculite, silicas, quartz powder, montmorillonite and mixtures thereof. Agriculturally acceptable adjuvants that promote sticking to the seed or other plant parts that can be added to the compositions include polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other useful agriculturally acceptable adjuvants that can promote coating of seeds or other plant parts include polymers and copolymers of vinyl acetate, polyvinylpyrrolidone-vinyl acetate copolymer and water-soluble waxes. These compositions can be maintained in a dry or semi dry form or can be formulated into slurries by addition of liquids as desired. The compositions can then be used to spray or coat the plants or seeds to obtain beneficial effects associated with application of *Methylobacterium* to plants.

Example 10. Titers of Various *Methylobacterium* in the Presence and Absence of Various Solids in the Media Fourteen strains in the genus *Methylobacterium* were purchased from the DSMZ (Braunschweig, Germany) and the ATCC (Manassas, Va., USA). These 14 strains consist of 12 different species, as there were three *M. extorquens* in the set:
1. DSM-6343 *Methylobacterium* extorquens
2. DSM-1819 *Methylobacterium* radiotolerans
3. DSM-13060 *Methylobacterium* extorquens
4. DSM-18172 *Methylobacterium* organophilum
5. DSM-1708 *Methylobacterium* mesophilicum
6. DSM-18207 *Methylobacterium* oryzae
7. DSM-19779 *Methylobacterium* phyllosphaerae
8. ATCC-14718 *Methylobacterium* extorquens
9. ATCC-14821 *Methylobacterium* rhodinum
10. ATCC-21611 *Methylobacterium* rhodesianum
11. ATCC-35065 *Methylobacterium* fujisawaense
12. ATCC-43883 *Methylobacterium* zatmanii
13. ATCC-51358 *Methylobacterium* aminovorans
14. ATCC-700647 *Methylobacterium* thiocyanatum For the tests below, the inocula came from cultures grown in water-clear AMS-GP medium. These cultures were grown in 200 ml of the water-clear AMS-GP medium, titered, and then concentrated ten-fold. These PPFM cultures, with no solid substrates present, were used to inoculate test tubes containing 10 ml of water-clear AMS-GP medium, or AMS-GP medium with various added solid substrates. 20 mg of the various solid substrates were added to each 10 ml tube, yielding a solid substrate concentration equivalent to 2 grams per liter. Titers are expressed throughout as Colony Forming Units per milliliter (CFU/mL). The target initial titer in each tube was about $1\times10^5$ PPFM colony forming units per ml. The inoculated test tubes were placed on a rotary shaker set and grown for three days at 30 degrees C. and 250 rpm. After three days of growth, the PPFM cultures were titered.

| Growth of PPFM strains in water-clear AMS-GP liquid medium | | | |
|---|---|---|---|
| | | initial titer | titer after 3 days |
| DSM-6343 | M. extorquens | $3.5 \times 10^5$ | $1.2 \times 10^6$ |
| DSM-1819 | M. radiotolerans | $1.8 \times 10^5$ | $1.3 \times 10^6$ |
| DSM-13060 | M. extorquens | $3.1 \times 10^5$ | $3.2 \times 10^5$ |
| DSM-18172 | M. organophilum | $1.4 \times 10^5$ | $1.8 \times 10^5$ |
| DSM-1708 | M. mesophilicum | $3.3 \times 10^5$ | $1.0 \times 10^5$ |
| DSM-18207 | M. oryzae | $1.1 \times 10^5$ | $2.2 \times 10^6$ |
| DSM-19779 | M. phyllosphaerae | $2.1 \times 10^5$ | $1.1 \times 10^6$ |
| ATCC-14718 | M. extorquens | $2.0 \times 10^5$ | $1.7 \times 10^5$ |
| ATCC-14821 | M. rhodinum | $4.4 \times 10^5$ | $2.9 \times 10^5$ |
| ATCC-21611 | M. rhodesianum | $1.8 \times 10^5$ | $1.4 \times 10^5$ |
| ATCC-35065 | M. fujisawaense | $1.3 \times 10^5$ | $1.9 \times 10^6$ |
| ATCC-43883 | M. zatmanii | $5.0 \times 10^5$ | $1.9 \times 10^5$ |
| ATCC-51358 | M. aminovorans | $9.5 \times 10^4$ | $1.7 \times 10^5$ |
| ATCC-700647 | M. thiocyanatum | $1.8 \times 10^5$ | $7.6 \times 10^4$ |

| Growth of PPFM strains in turbid AMS-GP liquid medium | | | |
|---|---|---|---|
| | | initial titer | titer after 3 days |
| DSM-6343 | M. extorquens | $2.5 \times 10^5$ | $2.1 \times 10^9$ |
| DSM-1819 | M. radiotolerans | $7.6 \times 10^4$ | $6.8 \times 10^8$ |
| DSM-13060 | M. extorquens | $1.9 \times 10^5$ | $4.4 \times 10^8$ |
| DSM-18172 | M. organophilum | $1.1 \times 10^5$ | $1.9 \times 10^9$ |
| DSM-1708 | M. mesophilicum | $1.4 \times 10^5$ | $9.3 \times 10^8$ |
| DSM-18207 | M. oryzae | $7.3 \times 10^4$ | $2.4 \times 10^8$ |
| DSM-19779 | M. phyllosphaerae | $1.8 \times 10^5$ | $7.5 \times 10^8$ |
| ATCC-14718 | M. extorquens | $9.3 \times 10^4$ | $2.0 \times 10^9$ |
| ATCC-14821 | M. rhodinum | $7.1 \times 10^4$ | $7.2 \times 10^8$ |
| ATCC-21611 | M. rhodesianum | $3.9 \times 10^5$ | $6.8 \times 10^8$ |
| ATCC-35065 | M. fujisawaense | $8.2 \times 10^4$ | $2.3 \times 10^8$ |
| ATCC-43883 | M. zatmanii | $1.8 \times 10^5$ | $6.2 \times 10^8$ |
| ATCC-51358 | M. aminovorans | $6.8 \times 10^4$ | $1.7 \times 10^9$ |
| ATCC-700647 | M. thiocyanatum | $4.3 \times 10^5$ | $6.5 \times 10^8$ |

| Growth of PPFM strains in AMS-GP liquid medium plus diatomaceous earth (at 2 grams per liter) | | | |
|---|---|---|---|
| | | initial titer | titer after 3 days |
| DSM-6343 | M. extorquens | $2.1 \times 10^5$ | $8.7 \times 10^8$ |
| DSM-1819 | M. radiotolerans | $1.1 \times 10^5$ | $3.3 \times 10^8$ |
| DSM-13060 | M. extorquens | $6.8 \times 10^4$ | $8.4 \times 10^8$ |
| DSM-18172 | M. organophilum | $3.1 \times 10^5$ | $8.1 \times 10^8$ |
| DSM-1708 | M. mesophilicum | $1.4 \times 10^5$ | $2.4 \times 10^9$ |

Growth of PPFM strains in AMS-GP liquid medium
plus diatomaceous earth (at 2 grams per liter)

|  |  | initial titer | titer after 3 days |
|---|---|---|---|
| DSM-18207 | M. oryzae | $2.1 \times 10^5$ | $3.1 \times 10^9$ |
| DSM-19779 | M. phyllosphaerae | $9.6 \times 10^4$ | $3.6 \times 10^8$ |
| ATCC-14718 | M. extorquens | $1.8 \times 10^5$ | $4.8 \times 10^8$ |
| ATCC-14821 | M. rhodinum | $8.0 \times 10^4$ | $5.9 \times 10^8$ |
| ATCC-21611 | M. rhodesianum | $3.5 \times 10^5$ | $7.7 \times 10^8$ |
| ATCC-35065 | M. fujisawaense | $1.5 \times 10^5$ | $9.2 \times 10^8$ |
| ATCC-43883 | M. zatmanii | $6.5 \times 10^4$ | $9.6 \times 10^8$ |
| ATCC-51358 | M. aminovorans | $3.0 \times 10^5$ | $2.7 \times 10^9$ |
| ATCC-700647 | M. thiocyanatum | $1.4 \times 10^5$ | $2.3 \times 10^9$ |

Growth of PPFM strains in AMS-GP liquid medium plus agar (at 2 grams per liter)

|  |  | initial titer | titer after 3 days |
|---|---|---|---|
| DSM-6343 | M. extorquens | $1.5 \times 10^5$ | $1.6 \times 10^8$ |
| DSM-1819 | M. radiotolerans | $1.3 \times 10^5$ | $3.7 \times 10^8$ |
| DSM-13060 | M. extorquens | $9.2 \times 10^4$ | $1.7 \times 10^8$ |
| DSM-18172 | M. organophilum | $8.1 \times 10^4$ | $9.3 \times 10^7$ |
| DSM-1708 | M. mesophilicum | $5.2 \times 10^5$ | $2.8 \times 10^8$ |
| DSM-18207 | M. oryzae | $1.9 \times 10^5$ | $5.0 \times 10^8$ |
| DSM-19779 | M. phyllosphaerae | $1.0 \times 10^5$ | $5.3 \times 10^8$ |
| ATCC-14718 | M. extorquens | $2.4 \times 10^5$ | $4.7 \times 10^8$ |
| ATCC-14821 | M. rhodinum | $1.5 \times 10^5$ | $5.1 \times 10^8$ |
| ATCC-21611 | M. rhodesianum | $8.1 \times 10^4$ | $4.3 \times 10^8$ |
| ATCC-35065 | M. fujisawaense | $1.0 \times 10^5$ | $4.4 \times 10^8$ |
| ATCC-43883 | M. zatmanii | $1.3 \times 10^5$ | $5.6 \times 10^8$ |
| ATCC-51358 | M. aminovorans | $4.5 \times 10^5$ | $6.4 \times 10^8$ |
| ATCC-700647 | M. thiocyanatum | $3.6 \times 10^5$ | $1.7 \times 10^8$ |

Growth of PPFM strains in AMS-GP liquid medium plus powdered kelp (at 2 grams per liter)

|  |  | initial titer | titer after 3 days |
|---|---|---|---|
| DSM-6343 | M. extorquens | $3.8 \times 10^5$ | $4.3 \times 10^8$ |
| DSM-1819 | M. radiotolerans | $9.1 \times 10^4$ | $4.1 \times 10^8$ |
| DSM-13060 | M. extorquens | $4.0 \times 10^5$ | $9.7 \times 10^7$ |
| DSM-18172 | M. organophilum | $2.2 \times 10^5$ | $2.8 \times 10^8$ |
| DSM-1708 | M. mesophilicum | $1.2 \times 10^5$ | $1.0 \times 10^8$ |
| DSM-18207 | M. oryzae | $9.4 \times 10^4$ | $6.4 \times 10^8$ |
| DSM-19779 | M. phyllosphaerae | $7.7 \times 10^4$ | $3.8 \times 10^8$ |
| ATCC-14718 | M. extorquens | $3.0 \times 10^5$ | $4.7 \times 10^8$ |
| ATCC-14821 | M. rhodinum | $8.4 \times 10^4$ | $1.6 \times 10^8$ |
| ATCC-21611 | M. rhodesianum | $9.7 \times 10^4$ | $4.1 \times 10^8$ |
| ATCC-35065 | M. fujisawaense | $8.2 \times 10^4$ | $3.4 \times 10^8$ |
| ATCC-43883 | M. zatmanii | $9.7 \times 10^4$ | $4.0 \times 10^8$ |
| ATCC-51358 | M. aminovorans | $2.6 \times 10^5$ | $6.3 \times 10^8$ |
| ATCC-700647 | M. thiocyanatum | $3.5 \times 10^5$ | $5.2 \times 10^8$ |

Growth of PPFM strains in AMS-GP liquid medium plus coconut husk fiber (at 2 grams per liter)

|  |  | initial titer | titer after 3 days |
|---|---|---|---|
| DSM-6343 | M. extorquens | $2.0 \times 10^5$ | $3.4 \times 10^8$ |
| DSM-1819 | M. radiotolerans | $2.1 \times 10^5$ | $6.0 \times 10^8$ |
| DSM-13060 | M. extorquens | $8.9 \times 10^4$ | $2.5 \times 10^8$ |
| DSM-18172 | M. organophilum | $8.5 \times 10^4$ | $7.5 \times 10^7$ |
| DSM-1708 | M. mesophilicum | $6.0 \times 10^4$ | $6.0 \times 10^8$ |
| DSM-18207 | M. oryzae | $1.9 \times 10^5$ | $3.2 \times 10^8$ |
| DSM-19779 | M. phyllosphaerae | $9.6 \times 10^4$ | $1.2 \times 10^8$ |
| ATCC-14718 | M. extorquens | $2.8 \times 10^5$ | $9.7 \times 10^7$ |
| ATCC-14821 | M. rhodinum | $3.5 \times 10^5$ | $8.9 \times 10^7$ |
| ATCC-21611 | M. rhodesianum | $7.4 \times 10^4$ | $8.2 \times 10^7$ |
| ATCC-35065 | M. fujisawaense | $6.1 \times 10^4$ | $7.0 \times 10^7$ |
| ATCC-43883 | M. zatmanii | $8.0 \times 10^4$ | $5.3 \times 10^8$ |
| ATCC-51358 | M. aminovorans | $3.3 \times 10^5$ | $2.5 \times 10^8$ |
| ATCC-700647 | M. thiocyanatum | $3.3 \times 10^5$ | $7.3 \times 10^7$ |

The coconut husk fiber was a product called "Hermit Soil", with the sole ingredient listed as "coconut fiber substrate" and sold by Zoo-Med Laboratories, Inc., of San Luis Obispo, Calif.

Growth of PPFM strains in AMS-GP liquid medium plus cottonseed meal (at 2 grams per liter)

|  |  | initial titer | titer after 3 days |
|---|---|---|---|
| DSM-6343 | M. extorquens | $1.0 \times 10^5$ | $4.0 \times 10^8$ |
| DSM-1819 | M. radiotolerans | $1.3 \times 10^5$ | $5.5 \times 10^8$ |
| DSM-13060 | M. extorquens | $8.9 \times 10^4$ | $4.7 \times 10^8$ |
| DSM-18172 | M. organophilum | $2.0 \times 10^5$ | $8.8 \times 10^7$ |
| DSM-1708 | M. mesophilicum | $7.9 \times 10^4$ | $5.8 \times 10^8$ |
| DSM-18207 | M. oryzae | $1.0 \times 10^5$ | $2.8 \times 10^8$ |
| DSM-19779 | M. phyllosphaerae | $4.1 \times 10^5$ | $9.0 \times 10^7$ |
| ATCC-14718 | M. extorquens | $9.5 \times 10^4$ | $7.9 \times 10^7$ |
| ATCC-14821 | M. rhodinum | $5.4 \times 10^5$ | $5.7 \times 10^8$ |
| ATCC-21611 | M. rhodesianum | $5.1 \times 10^5$ | $2.7 \times 10^8$ |
| ATCC-35065 | M. fujisawaense | $8.1 \times 10^4$ | $5.9 \times 10^8$ |
| ATCC-43883 | M. zatmanii | $7.6 \times 10^4$ | $3.9 \times 10^8$ |
| ATCC-51358 | M. aminovorans | $2.7 \times 10^5$ | $8.3 \times 10^7$ |
| ATCC-700647 | M. thiocyanatum | $4.6 \times 10^5$ | $4.4 \times 10^8$ |

Growth of PPFM strains in AMS-GP liquid medium plus bone meal (at 2 grams per liter)

|  |  | initial titer | titer after 3 days |
|---|---|---|---|
| DSM-6343 | M. extorquens | $9.6 \times 10^4$ | $1.4 \times 10^8$ |
| DSM-1819 | M. radiotolerans | $4.7 \times 10^5$ | $5.0 \times 10^8$ |
| DSM-13060 | M. extorquens | $8.5 \times 10^4$ | $4.7 \times 10^8$ |
| DSM-18172 | M. organophilum | $5.9 \times 10^4$ | $3.9 \times 10^8$ |
| DSM-1708 | M. mesophilicum | $8.2 \times 10^4$ | $2.6 \times 10^8$ |
| DSM-18207 | M. oryzae | $3.6 \times 10^5$ | $4.5 \times 10^8$ |
| DSM-19779 | M. phyllosphaerae | $5.4 \times 10^4$ | $8.0 \times 10^7$ |
| ATCC-14718 | M. extorquens | $1.5 \times 10^5$ | $9.1 \times 10^7$ |
| ATCC-14821 | M. rhodinum | $9.9 \times 10^4$ | $7.0 \times 10^7$ |
| ATCC-21611 | M. rhodesianum | $1.6 \times 10^5$ | $8.1 \times 10^7$ |
| ATCC-35065 | M. fujisawaense | $6.9 \times 10^4$ | $2.0 \times 10^8$ |
| ATCC-43883 | M. zatmanii | $5.7 \times 10^4$ | $6.9 \times 10^7$ |
| ATCC-51358 | M. aminovorans | $9.9 \times 10^4$ | $4.3 \times 10^8$ |
| ATCC-700647 | M. thiocyanatum | $1.9 \times 10^5$ | $1.5 \times 10^8$ |

Growth of PPFM strains in AMS-GP liquid medium plus blood meal (at 2 grams per liter)

|  |  | initial titer | titer after 3 days |
|---|---|---|---|
| DSM-6343 | M. extorquens | $7.7 \times 10^4$ | $7.0 \times 10^8$ |
| DSM-1819 | M. radiotolerans | $7.9 \times 10^4$ | $8.8 \times 10^7$ |
| DSM-13060 | M. extorquens | $4.4 \times 10^5$ | $6.7 \times 10^7$ |
| DSM-18172 | M. organophilum | $3.1 \times 10^5$ | $8.4 \times 10^7$ |
| DSM-1708 | M. mesophilicum | $1.0 \times 10^5$ | $4.0 \times 10^8$ |
| DSM-18207 | M. oryzae | $3.9 \times 10^5$ | $5.0 \times 10^8$ |
| DSM-19779 | M. phyllosphaerae | $2.5 \times 10^5$ | $8.0 \times 10^7$ |
| ATCC-14718 | M. extorquens | $9.5 \times 10^4$ | $9.5 \times 10^7$ |
| ATCC-14821 | M. rhodinum | $6.8 \times 10^4$ | $8.6 \times 10^7$ |
| ATCC-21611 | M. rhodesianum | $7.4 \times 10^4$ | $4.9 \times 10^7$ |

Growth of PPFM strains in AMS-GP liquid medium plus blood meal (at 2 grams per liter)

| | | initial titer | titer after 3 days |
|---|---|---|---|
| ATCC-35065 | M. fujisawaense | $2.6 \times 10^5$ | $2.0 \times 10^8$ |
| ATCC-43883 | M. zatmanii | $3.2 \times 10^5$ | $4.3 \times 10^8$ |
| ATCC-51358 | M. aminovorans | $7.0 \times 10^4$ | $1.8 \times 10^8$ |
| ATCC-700647 | M. thiocyanatum | $3.2 \times 10^5$ | $5.5 \times 10^7$ |

Growth of PPFM strains in AMS-GP liquid medium plus sand (at 2 grams per liter)

| | | initial titer | titer after 3 days |
|---|---|---|---|
| DSM-6343 | M. extorquens | $1.8 \times 10^5$ | $3.2 \times 10^8$ |
| DSM-1819 | M. radiotolerans | $1.4 \times 10^5$ | $1.9 \times 10^8$ |
| DSM-13060 | M. extorquens | $1.1 \times 10^5$ | $6.0 \times 10^8$ |
| DSM-18172 | M. organophilum | $2.8 \times 10^5$ | $4.8 \times 10^8$ |
| DSM-1708 | M. mesophilicum | $7.8 \times 10^4$ | $1.6 \times 10^8$ |
| DSM-18207 | M. oryzae | $5.2 \times 10^5$ | $3.2 \times 10^8$ |
| DSM-19779 | M. phyllosphaerae | $2.5 \times 10^5$ | $9.7 \times 10^7$ |
| ATCC-14718 | M. extorquens | $9.7 \times 10^4$ | $4.4 \times 10^8$ |
| ATCC-14821 | M. rhodinum | $2.7 \times 10^5$ | $9.2 \times 10^7$ |
| ATCC-21611 | M. rhodesianum | $9.7 \times 10^4$ | $6.4 \times 10^8$ |
| ATCC-35065 | M. fujisawaense | $5.7 \times 10^4$ | $9.1 \times 10^7$ |
| ATCC-43883 | M. zatmanii | $8.2 \times 10^4$ | $3.9 \times 10^8$ |
| ATCC-51358 | M. aminovorans | $8.8 \times 10^4$ | $1.8 \times 10^8$ |
| ATCC-700647 | M. thiocyanatum | $9.8 \times 10^4$ | $6.7 \times 10^8$ |

The sand was a product called "White Hermit Crab Sand", with the ingredients listed as calcium carbonate and magnesium carbonate, and sold by Zoo-Med Laboratories, Inc., of San Luis Obispo, Calif.

Growth of PPFM strains in AMS-GP liquid medium plus a silica-micaceous clay (at 2 grams per liter)

| | | initial titer | titer after 3 days |
|---|---|---|---|
| DSM-6343 | M. extorquens | $9.8 \times 10^4$ | $9.4 \times 10^8$ |
| DSM-1819 | M. radiotolerans | $2.4 \times 10^5$ | $1.2 \times 10^8$ |
| DSM-13060 | M. extorquens | $5.4 \times 10^5$ | $2.8 \times 10^8$ |
| DSM-18172 | M. organophilum | $2.3 \times 10^5$ | $6.0 \times 10^8$ |
| DSM-1708 | M. mesophilicum | $8.3 \times 10^4$ | $5.5 \times 10^8$ |
| DSM-18207 | M. oryzae | $9.7 \times 10^4$ | $3.2 \times 10^8$ |
| DSM-19779 | M. phyllosphaerae | $6.6 \times 10^4$ | $9.8 \times 10^8$ |
| ATCC-14718 | M. extorquens | $1.2 \times 10^5$ | $5.5 \times 10^8$ |
| ATCC-14821 | M. rhodium | $4.8 \times 10^5$ | $6.5 \times 10^8$ |
| ATCC-21611 | M. rhodesiamun | $2.0 \times 10^5$ | $5.2 \times 10^8$ |
| ATCC-35065 | M. fujisawaense | $6.2 \times 10^4$ | $1.0 \times 10^9$ |
| ATCC-43883 | M. zatmanii | $3.1 \times 10^5$ | $9.0 \times 10^7$ |
| ATCC-51358 | M. aminovorans | $4.3 \times 10^5$ | $3.2 \times 10^8$ |
| ATCC-700647 | M. thiocyanatum | $7.6 \times 10^4$ | $8.0 \times 10^8$ |

The micaceous clay was a product called "Profile", with the ingredients listed as a blend of silica and illite. Illite is a micaceous clay. Profile is sold by Profile Products, LLC, of Buffalo Grove, Ill.

Growth of PPFM strains in AMS-GP liquid medium plus a silicate-mineraloid clay (at 2 grams per liter)

| | | initial titer | titer after 3 days |
|---|---|---|---|
| DSM-6343 | M. extorquens | $3.5 \times 10^4$ | $4.0 \times 10^8$ |
| DSM-1819 | M. radiotolerans | $2.5 \times 10^5$ | $5.0 \times 10^8$ |
| DSM-13060 | M. extorquens | $5.2 \times 10^4$ | $8.1 \times 10^8$ |
| DSM-18172 | M. organophilum | $4.3 \times 10^5$ | $5.6 \times 10^8$ |
| DSM-1708 | M. mesophilicum | $1.0 \times 10^5$ | $2.0 \times 10^9$ |
| DSM-18207 | M. oryzae | $2.2 \times 10^5$ | $8.2 \times 10^8$ |
| DSM-19779 | M. phyllosphaerae | $3.6 \times 10^5$ | $6.6 \times 10^8$ |
| ATCC-14718 | M. extorquens | $2.4 \times 10^5$ | $4.1 \times 10^8$ |
| ATCC-14821 | M. rhodinum | $3.4 \times 10^5$ | $1.3 \times 10^9$ |
| ATCC-21611 | M. rhodesianum | $3.8 \times 10^5$ | $7.0 \times 10^8$ |
| ATCC-35065 | M. fujisawaense | $5.5 \times 10^4$ | $5.4 \times 10^8$ |
| ATCC-43883 | M. zatmanii | $6.9 \times 10^4$ | $3.0 \times 10^8$ |
| ATCC-51358 | M. aminovorans | $7.8 \times 10^4$ | $1.9 \times 10^9$ |
| ATCC-700647 | M. thiocyanatum | $4.2 \times 10^5$ | $4.8 \times 10^8$ |

The mineraloid clay was a product called "Rare Earth", with the ingredients listed as a blend of a pyrophyllitic silicate clay and leonardite. Leonardite is a mineraloid composed of oxidized lignite; it is high in humic acid. Rare Earth is sold by General Hydroponics of Sebastopol, Calif.

Growth of PPFM strains in AMS-GP liquid medium plus an aluminum phyllosilicate clay (at 2 grams per liter)

| | | initial titer | titer after 3 days |
|---|---|---|---|
| DSM-6343 | M. extorquens | $3.5 \times 10^5$ | $8.0 \times 10^8$ |
| DSM-1819 | M. radiotolerans | $2.5 \times 10^5$ | $6.1 \times 10^8$ |
| DSM-13060 | M. extorquens | $5.2 \times 10^5$ | $5.5 \times 10^8$ |
| DSM-18172 | M. organophilum | $4.3 \times 10^5$ | $8.2 \times 10^7$ |
| DSM-1708 | M. mesophilicum | $1.0 \times 10^5$ | $1.3 \times 10^9$ |
| DSM-18207 | M. oryzae | $2.2 \times 10^5$ | $9.6 \times 10^8$ |
| DSM-19779 | M. phyllosphaerae | $3.6 \times 10^5$ | $2.7 \times 10^8$ |
| ATCC-14718 | M. extorquens | $3.0 \times 10^5$ | $7.8 \times 10^8$ |
| ATCC-14821 | M. rhodinum | $3.4 \times 10^5$ | $6.5 \times 10^8$ |
| ATCC-21611 | M. rhodesianum | $2.4 \times 10^5$ | $2.8 \times 10^9$ |
| ATCC-35065 | M. fujisawaense | $9.9 \times 10^4$ | $2.2 \times 10^9$ |
| ATCC-43883 | M. zatmanii | $2.3 \times 10^5$ | $7.2 \times 10^8$ |
| ATCC-51358 | M. aminovorans | $3.8 \times 10^5$ | $6.3 \times 10^8$ |
| ATCC-700647 | M. thiocyanatum | $8.1 \times 10^4$ | $8.8 \times 10^8$ |

The aluminum phyllosilicate clay was a product called "Bentonite", with the ingredient listed an aluminum phyllosilicate clay. Bentonite is sold by L. D. Carlson Co. of Kent, Ohio.

Growth of PPFM strains in AMS-GP liquid medium plus crushed egg shell (at 2 grams per liter)

| | | initial titer | titer after 3 days |
|---|---|---|---|
| DSM-6343 | M. extorquens | $2.8 \times 10^5$ | $2.9 \times 10^9$ |
| DSM-1819 | M. radiotolerans | $2.1 \times 10^5$ | $7.4 \times 10^8$ |
| DSM-13060 | M. extorquens | $3.3 \times 10^5$ | $6.4 \times 10^8$ |
| DSM-18172 | M. organophilum | $4.5 \times 10^5$ | $8.7 \times 10^8$ |
| DSM-1708 | M. mesophilicum | $4.3 \times 10^5$ | $2.5 \times 10^9$ |
| DSM-18207 | M. oryzae | $2.3 \times 10^5$ | $9.3 \times 10^8$ |
| DSM-19779 | M. phyllosphaerae | $3.1 \times 10^5$ | $1.7 \times 10^9$ |
| ATCC-14718 | M. extorquens | $2.4 \times 10^5$ | $3.3 \times 10^9$ |
| ATCC-14821 | M. rhodinum | $4.2 \times 10^5$ | $7.8 \times 10^8$ |
| ATCC-21611 | M. rhodesianum | $8.4 \times 10^4$ | $5.7 \times 10^8$ |
| ATCC-35065 | M. fujisawaense | $1.1 \times 10^5$ | $2.8 \times 10^9$ |
| ATCC-43883 | M. zattmanii | $3.2 \times 10^5$ | $6.9 \times 10^8$ |
| ATCC-51358 | M. aminovorans | $2.8 \times 10^5$ | $6.7 \times 10^8$ |
| ATCC-700647 | M. thiocyanatum | $8.9 \times 10^4$ | $9.2 \times 10^8$ |

The crushed shell was obtained from chicken egg shells.
Four other solid substrates were tested with two PPFM strains. While all four of these solid substrates enabled the two PPFM strains to grow to higher titers than in water-clear AMS-GP medium, the growth was relatively light compared to the other solid substrates tested above. The ground wheat and ground barley were very coarse, which could have contributed to this relatively light growth due to the relatively low surface area of a coarsely ground solid substrate.

Because of this relatively light growth, these four solid substrates were not tested with the other PPFM strains.

| Growth of PPFM strains in AMS-GP liquid medium plus flax seed meal (at 2 grams per liter) | | | |
|---|---|---|---|
| | | initial titer | titer after 3 days |
| DSM-6343 | M. extorquens | $3.4 \times 10^5$ | $6.4 \times 10^6$ |
| DSM-1708 | M. mesophilicum | $9.9 \times 10^4$ | $1.2 \times 10^7$ |

| Growth of PPFM strains in AMS-GP liquid medium plus ground wheat (at 2 grams per liter) | | | |
|---|---|---|---|
| | | initial titer | titer after 3 days |
| DSM-6343 | M. exlorquens | $2.1 \times 10^5$ | $9.7 \times 10^6$ |
| DSM-1708 | M. mesophilicum | $4.3 \times 10^5$ | $3.3 \times 10^7$ |

| Growth of PPFM strains in AMS-GP liquid medium plus ground barley (at 2 grams per liter) | | | |
|---|---|---|---|
| | | initial titer | titer after 3 days |
| DSM-6343 | M. extorquens | $2.2 \times 10^5$ | $3.4 \times 10^7$ |
| DSM-1708 | M. mesophilicum | $9.2 \times 10^4$ | $1.4 \times 10^7$ |

| Growth of PPFM strains in AMS-GP liquid medium plus dried shrimp (at 2 grams per liter) | | | |
|---|---|---|---|
| | | initial titer | titer after 3 days |
| DSM-6343 | M. extorquens | $3.0 \times 10^5$ | $7.5 \times 10^6$ |
| DSM-1708 | M. mesophilicum | $7.1 \times 10^4$ | $3.7 \times 10^7$ |

The dried shrimp were powdered brine shrimp, sold by OmegaSea Ltd, of Sitka, Ak.

Example 11. Utilization of PPFM Bacteria to Promote Plant Growth and Early Development The establishment of a vigorous and uniform stand of corn plants early in the growing season is essential to a high yielding crop, and is mainly dependent on the development of a vigorous nodal root system. The first roots that emerge from a corn seed (the radicle and seminal roots) function mainly in the uptake of water from the soil. The radicle seminal roots do not provide other nourishment, which early in the growth of the seedling is provided by energy and nutrient reserves in the kernel. When nodal roots emerge from the corn stem, growth of the seminal roots slows dramatically and they contribute little to the season-long maintenance of the corn plant. Instead, the nodal root system plays this role. Thus, the early and vigorous establishment of a nodal root system plays a key role in the development of a uniform stand of corn. Failure to do so results in stunted plants and other deficiencies that end in lower yields at harvest.

Cultures of PPFM bacteria produced by the method of Example 3 (i.e. by growing the PPFM bacteria in liquid media containing insoluble salt crystals) were used to treat corn seeds. To 72 corn seeds, 20 milliliters of the PPFM culture were added, in a container such that the corn seeds were completely immersed in the PPFM culture. As a control, an equal number of corn seeds were immersed in the PPFM-free culture medium of Example 3. The corn seeds were soaked in these solutions for 4 hours, at room temperature (about 22 degrees C.), with gentle agitation. At the end of this soaking period, the seeds were planted in potting soil and allowed to germinate and grow for 8 days. At that time, the corn seedlings were dug up, rinsed to remove the soil, and the nodal roots counted and measured. The results are shown below.

| | control | PPFM treated | |
|---|---|---|---|
| number of nodal roots per plant, in milligrams | 2.56 | 2.88 | 13% more |
| average length of nodal roots per plant in centimeters | 2.33 | 3.44 | 48% longer |

These results indicate that contacting corn seeds with the high-titer PPFM culture provided by the instant invention results in the earlier emergence and more rapid growth of nodal roots.

Example 12. Growth of *Methylobacterium* in Liquid Media with Non-Particulate Solid Substances Ten distinct *Methylobacterium* (PPFM) strains were grown in 200 ml of the water-clear AMS-GP medium, titered, and then concentrated ten-fold. These PPFM cultures, with no solid substances present, were used to inoculate test tubes containing 10 ml of water-clear AMS-GP medium with various added non-particulate solid substances. For the non-particulate solids, 20 mg of the various non-particulate solid substances were added to each 10 ml tube, yielding a non-particulate solid substrate concentration equivalent to 2 grams per liter. The target initial titer in each tube was about $1 \times 10^5$ PPFM cells per ml. The inoculated test tubes were placed on a rotary shaker set and grown for three days at 30 degrees C. and 250 rpm.

| Growth of PPFM strains in AMS-GP liquid medium plus tufts of cotton (at 2 grams per liter) | | | |
|---|---|---|---|
| | | initial titer | titer after 3 days (CFU/mL) |
| DSM-6343 | M. exlorquens | $6.6 \times 10^4$ | $3.7 \times 10^8$ |
| DSM-1819 | M. radiotolerans | $2.4 \times 10^5$ | $1.2 \times 10^8$ |
| DSM-13060 | M. extorquens | $1.7 \times 10^5$ | $5.7 \times 10^7$ |
| DSM-18207 | M. oryzae | $1.6 \times 10^5$ | $9.4 \times 10^7$ |
| DSM-19779 | M. phyllosphaerae | $8.3 \times 10^4$ | $4.7 \times 10^8$ |
| ATCC-14718 | M. extorquens | $7.0 \times 10^4$ | $8.1 \times 10^7$ |
| ATCC-21611 | M. rhodesianum | $3.5 \times 10^5$ | $6.5 \times 10^7$ |
| ATCC-35065 | M. fujisawaense | $3.3 \times 10^5$ | $2.5 \times 10^8$ |
| ATCC-51358 | M. aminovorans | $4.2 \times 10^5$ | $7.0 \times 10^7$ |
| ATCC-700647 | M. thiocyanatum | $2.1 \times 10^5$ | $7.4 \times 10^7$ |

Figure 3:
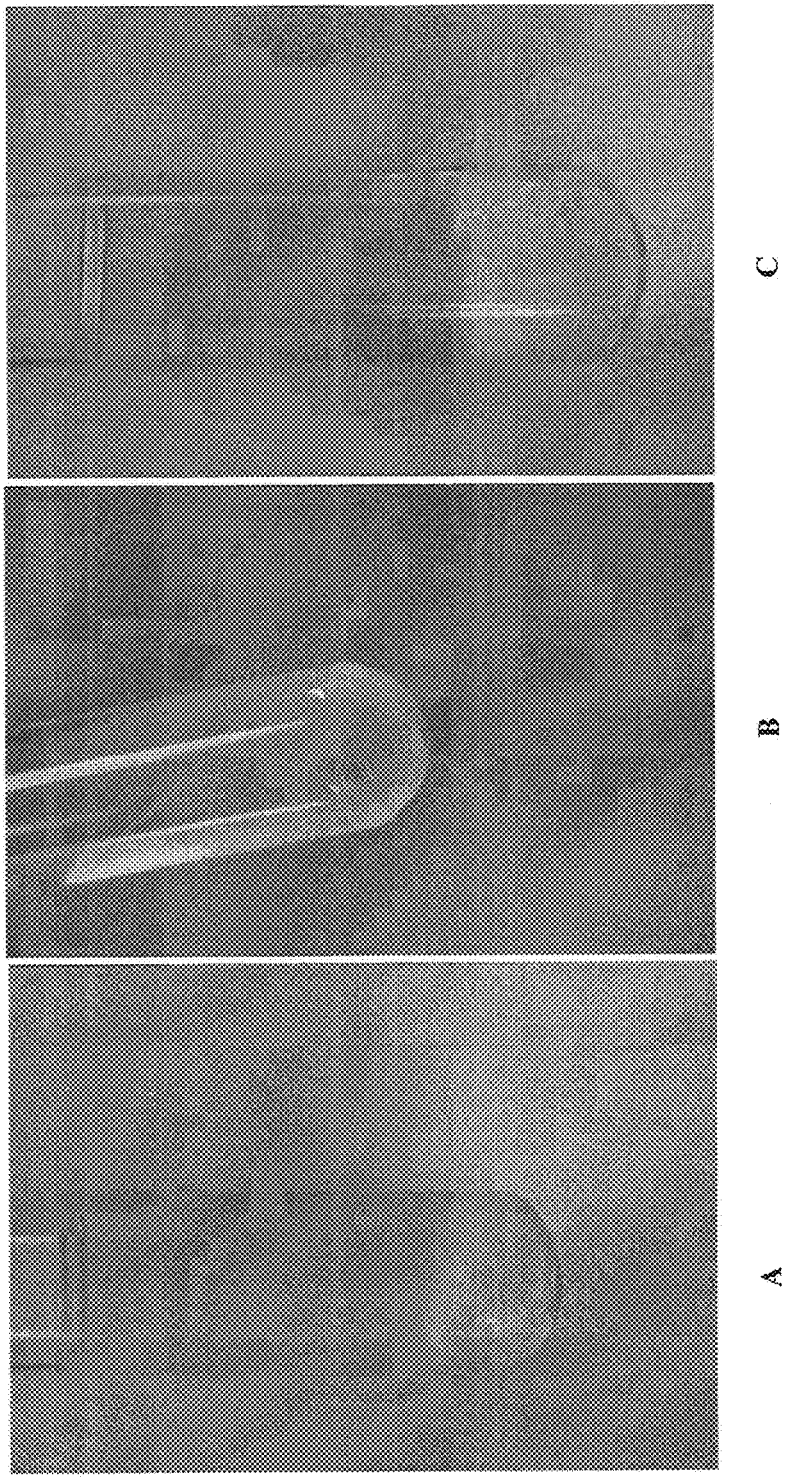
FIG. 3 A, B, C are photographs of test tubes containing liquid media with non-particulate solid substances with adherent *Methylobacterium*. In 3A, liquid media containing cotton tufts with adherent *Methylobacterium* that impart a dark pink color to the cotton are shown. In 3B, liquid media containing glass wool with adherent *Methylobacterium* that impart a pink color to the glass wool are shown. In 3C, liquid media containing body scrub material with adherent *Methylobacterium* that impart a pink color to the body scrub material are shown. The *Methylobacterium* strain is DSM-6343 *Methylobacterium* extorquens.
Figure 4:
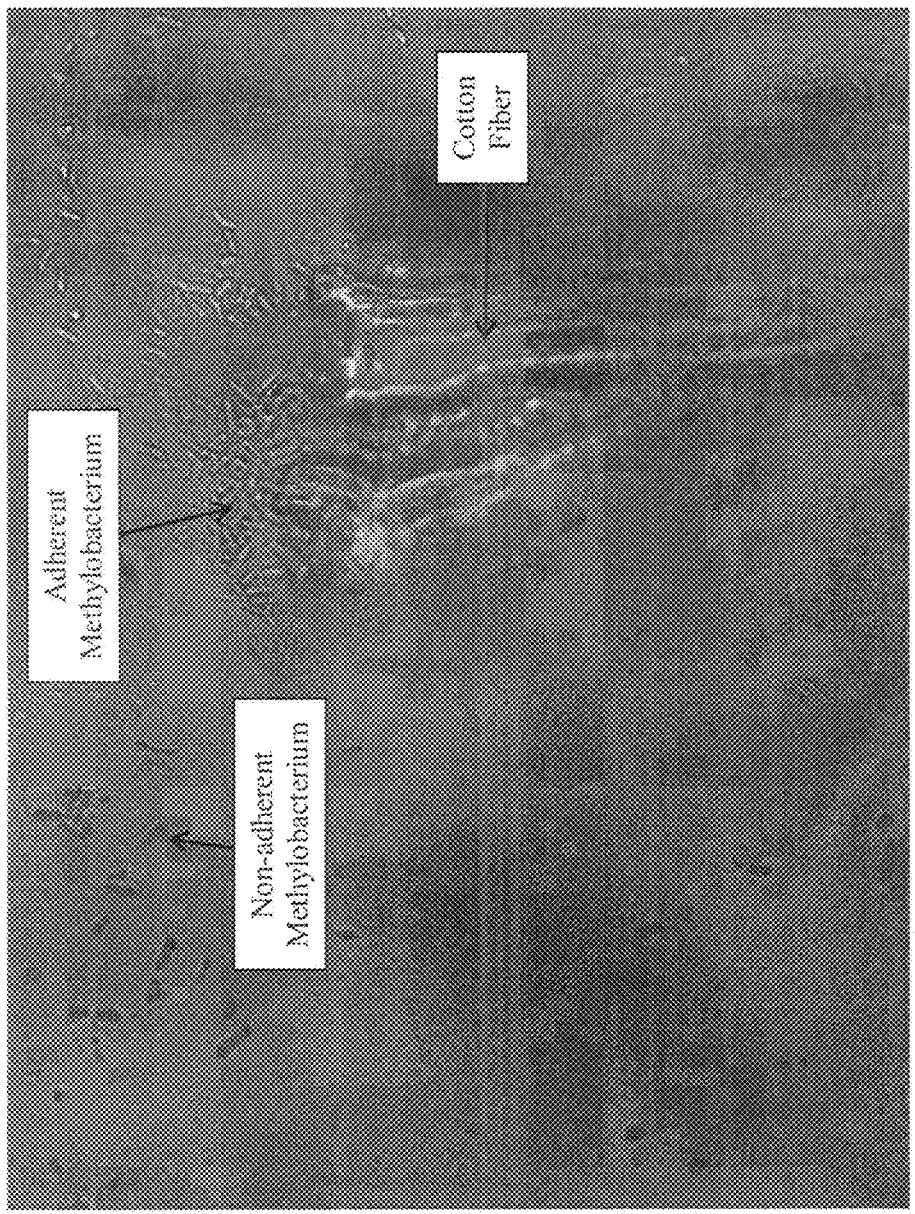
FIG. 4 is a photomicrograph of a showing PPFM strain ATCC-35065 *M. fujisawaense* adhered to cotton fibers. The cotton fibers, adherent *Methylobacterium*, and non-adherent *Methylobacterium* are indicated by the labels in the photomicrograph.

After three days of growth, the cotton tufts were a dark brilliant pink in color, being coated with adhered PPFM cells (FIG. 3A). These adhered PPFM were removed by vigorous vortexing, and the resulting suspensions of PPFM cells were titered. The titers of PPFM cells attained were higher than those attained by growing the PPFM in clear AMS-GP liquid medium (see representative results of Example 10 where PPFM grown for 3 days in water clear AMS-GP media did not exceed $10^6$ colony forming units per ml). A photomicrograph showing PPFM strain ATCC-35065 *M. fujisawaense* adhered to cotton fibers is provided in FIG. 4.

a. Growth of PPFM strains in AMS-GP liquid medium plus tufts of glass wool (at 2 grams per liter)

|  |  | initial titer | titer after 3 days (CFU/mL) |
|---|---|---|---|
| DSM-6343 | *M. extorquens* | $3.4 \times 10^5$ | $2.0 \times 10^8$ |
| DSM-1819 | *M. radiolerans* | $1.9 \times 10^5$ | $2.3 \times 10^8$ |
| DSM-13060 | *M. extorquens* | $8.0 \times 10^4$ | $5.6 \times 10^7$ |
| DSM-18207 | *M. oryzae* | $9.4 \times 10^4$ | $1.8 \times 10^8$ |
| DSM-19779 | *M. phyllosphaerae* | $3.8 \times 10^5$ | $6.5 \times 10^7$ |
| ATCC-14718 | *M. extorquens* | $7.4 \times 10^4$ | $3.9 \times 10^8$ |
| ATCC-21611 | *M. rhodesianum* | $3.2 \times 10^5$ | $8.0 \times 10^7$ |
| ATCC-35065 | *M. fujisawaense* | $6.8 \times 10^4$ | $1.0 \times 10^8$ |
| ATCC-51358 | *M. aminovorans* | $1.1 \times 10^5$ | $6.5 \times 10^7$ |
| ATCC-700647 | *M. thiocyanatum* | $1.7 \times 10^5$ | $3.0 \times 10^8$ |

After three days of growth, the glass wool tufts were brilliant pink in color, being coated with adhered PPFM cells (FIG. 3B). These adhered PPFM were removed by vigorous vortexing, and the resulting suspensions of PPFM cells were titered. The titers of PPFM cells attained were higher than those attained by growing the PPFM in clear AMS-GP liquid medium (see representative results of Example 2). The titers of PPFM cells attained were higher than those attained by growing the PPFM in clear AMS-GP liquid medium (see representative results of Example 10 where PPFM grown for 3 days in water clear AMS-GP media did not exceed $10^6$ colony forming units per ml).

b. Growth of PPFM strains in AMS-GP liquid medium plus tufts of synthetic sponge (at 2 grams per liter)

|  |  | initial titer | titer after 3 days (CFU/mL) |
|---|---|---|---|
| DSM-6343 | *M. extorquens* | $8.6 \times 10^4$ | $8.4 \times 10^7$ |
| DSM-1819 | *M. radiotolerans* | $4.0 \times 10^5$ | $4.4 \times 10^7$ |
| DSM-13060 | *M. extorquens* | $8.4 \times 10^4$ | $2.9 \times 10^8$ |
| DSM-18207 | *M. oryzae* | $9.2 \times 10^4$ | $3.4 \times 10^8$ |
| DSM-19779 | *M. phyllosphaerae* | $9.0 \times 10^4$ | $5.7 \times 10^7$ |
| ATCC-14718 | *M. extorquens* | $7.5 \times 10^4$ | $3.2 \times 10^8$ |
| ATCC-21611 | *M. rhodesianum* | $8.5 \times 10^4$ | $1.6 \times 10^8$ |
| ATCC-35065 | *M. fujisawaense* | $3.4 \times 10^5$ | $7.5 \times 10^7$ |
| ATCC-51358 | *M. aminovorans* | $7.8 \times 10^4$ | $7.8 \times 10^7$ |
| ATCC-700647 | *M. thiocyanatum* | $2.4 \times 10^5$ | $9.5 \times 10^7$ |

The synthetic sponge used was "Body Scrub", manufactured by Compac Industries, Inc. of Decatur, Ga. The synthetic sponge is made of a polyester polymeric material.

After three days of growth, the synthetic sponge tufts were brilliant pink in color, being coated with adhered PPFM cells (FIG. 3C). These adhered PPFM were removed by vigorous vortexing, and the resulting suspensions of PPFM cells were titered. The titers of PPFM cells attained were higher than those attained by growing the PPFM in clear AMS-GP liquid medium (see representative results of Example 10 where PPFM grown for 3 days in water clear AMS-GP media did not exceed 106 colony forming units per ml).

REFERENCES

Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.

Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.

Corpe, W. A., and D. V. Basile. 1982. Methanol-utilizing bacteria associated with green plants. Devel. Industr. Microbiol. 23: 483-493.

Corpe, W. A., and S. Rheem. 1989. Ecology of the methylotrophic bacteria on living leaf surfaces. FEMS Microbiol. Ecol. 62: 243-250.

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

Holland, M. A. 1997. *Methylobacterium* and plants. Recent. Res. Devel. in Plant Physiol. 1: 207-213.

Holland, M. A., and J. C. Polacco. 1994. PPFMs and other covert contaminants: Is there more to plant physiology than just plant? Annu. Rev. Plant Physiol. Plant Mol. Biol. 45: 197-209.

Kutschera, U. 2007. Plant-associated methylobacteria as co-evolved phytosymbionts. A hypothesis. Plant Signal Behav. 2: 74-78.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.

Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar CO-47 (*Oryza sativa* L.) by *Methylobacterium* spp. Bot. Bull. Acad. Sin. 45: 315-324.

Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10):1645-54.

Stanier, R. Y., N. J. Palleroni, and M. Doudoroff. 1966. The aerobic pseudomonads: A taxonomic study. J. Gen. Microbiol. 43: 159-271.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220.

Sy, A., A. C. J. Timmers, C. Knief, and J. A. Vorholt. 2005. Methylotrophic metabolism is advantageous for *Methylo-* bacterium extorquens during colonization of *Medicago truncatula* under competitive conditions. Appl. Environ. Microbiol. 71: 7245-7252.

Vogel, H. J., and D. M. Bonner. 1956. Acetylornithinase ofEscherichia coi: Partial purification and some properties. J. Biol. Chem. 218: 97-106.

Whittenbury, R., S. L. Davies, and J. F. Wilkinson. 1970. Enrichment, isolation and some properties of methane-utilizing bacteria. J. Gen. Microbiol. 61: 205-218.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for obtaining a *Methylobacterium* preparation comprising:
    preparing a culture medium comprising a mono-culture or co-culture of *Methylobacterium*, wherein said medium comprises a liquid phase and a solid phase, wherein the liquid and solid phase are provided as sterile components, wherein the solid phase comprises a plurality of particles which are suspended in the liquid phase, wherein the particles are about 1 micron to about 1000 microns in average length or average diameter, and wherein the solid phase does not comprise viable photosynthetic microorganisms;
    (ii) growing said *Methylobacterium* from an initial titer in said culture medium, wherein said culture medium is essentially free of microorganisms other than *Methylobacterium*, wherein said particles provide for a decrease in doubling time of said *Methylobacterium* grown in said culture medium relative to the doubling time of the *Methylobacterium* grown in liquid media alone, and wherein the *Methylobacterium* titer in said culture medium is increased at least ten-fold relative to the initial titer of the *Methylobacterium* in the culture medium;
    (iii) producing a fermentation broth with a *Methylobacterium* titer of at least $5 \times 10^8$ colony-forming units per milliliter; and
    (iv) harvesting the *Methylobacterium* from said fermentation broth, thereby obtaining the *Methylobacterium* preparation.

2. The method of claim 1, wherein said method comprises the further step of drying the harvested *Methylobacterium*.

3. The method of claim 2, wherein drying is effected by spray drying, lyophilization, desiccation, heating, and combinations thereof.

4. The method of claim 1, wherein the titer of said *Methylobacterium* strain is increased at least 100-fold relative to the initial titer of the *Methylobacterium* in the culture medium.

5. The method of claim 1, wherein the particles are about 2 microns to about 1000 microns in average length or average diameter.

6. The method of claim 1, wherein said solid phase comprises about 0.02% to about 20% of said medium by mass.

7. The method of claim 1, wherein said solid phase comprises about 0.02% to about 0.5% of said medium by mass.

8. The method of claim 1, wherein at least 99.9% of the microorganisms present in the fermentation broth are *Methylobacterium*.

9. The method of claim 1, wherein said solid phase provides for adherent growth of said *Methylobacterium* and/or wherein said solid phase does not serve as a carbon source for said *Methylobacterium*.

10. The method of claim 1, wherein said solid phase comprises salt crystals.

11. The method of claim 10, wherein said salt crystals are insoluble or only partially soluble carbonates, chromates, sulfites, phosphates, hydroxides, oxides, and sulfides.

12. The method of claim 1, wherein said solid phase comprises a polysaccharide.

13. The method of claim 1, wherein said *Methylobacterium* is selected from the group consisting of *M aminovorans, M chloromethanicum, M dichloromethanicum, M extorquens, M fujisawaense, M mesophilicum, M organophilum, M radiotolerans, M rhodesianum, M rhodinum, M thiocyanatum, M nodulans, M cerastii, M gossipiicola, Methylobacterium* sp. strain LMG6378, *M phyllosphaerae, M oryzae, M platani, M populi*, and *M zatmanii*.

14. The method of claim 1, wherein the *Methylobacterium* titer in said culture medium is increased at least 1,000-fold relative to the initial titer of the *Methylobacterium* in the culture medium.

15. The method of claim 10, wherein said salt crystals are magnesium phosphate and/or calcium phosphate.

16. The method of claim 1, wherein said solid phase comprises diatomaceous earth.

17. The method of claim 12, wherein said polysaccharide is selected from the group consisting of a cellulosic polysaccharide, a chitinous polysaccharide, and a galactan polysaccharide.

18. The method of claim 1, wherein said liquid phase further comprises a carbon source supporting the growth of said *Methylobacterium*.

* * * * *